United States Patent [19]

Fischer et al.

[11] Patent Number: 5,677,449
[45] Date of Patent: Oct. 14, 1997

[54] SUBSTITUTED 1-H-3-ARYL-PYRROLIDINE-2,4-DIONE DERIVATIVES

[75] Inventors: Reiner Fischer, Monheim; Thomas Bretschneider, Siegburg; Bernd-Wieland Krüger, Bergisch Gladbach; Christoph Erdelen, Leichlingen; Hans-Joachim Santel, Leverkusen; Klaus Lürssen; Robert R. Schmidt, both of Bergisch Gladbach; Ulrike Wachendorff-Neumann, Monheim; Wilhelm Stendel, Wuppertal, all of Germany

[73] Assignee: Bayer Aktiengesellschaft, Leverkusen, Germany

[21] Appl. No.: 462,488

[22] Filed: Jun. 5, 1995

Related U.S. Application Data

[62] Division of Ser. No. 140,635, Oct. 21, 1993, Pat. No. 5,462,913.

[30] Foreign Application Priority Data

Oct. 28, 1992 [DE] Germany .................. 42 36 401.9
Aug. 11, 1993 [DE] Germany .................. 43 26 909.5

[51] Int. Cl.$^6$ .................. C07D 295/12; C07D 295/22
[52] U.S. Cl. .................. 544/165; 546/335; 560/45
[58] Field of Search .................. 560/43, 45; 544/165; 546/335

[56] References Cited

U.S. PATENT DOCUMENTS

| | | | |
|---|---|---|---|
| 4,584,303 | 4/1986 | Huang et al. | 514/326 |
| 5,462,913 | 10/1995 | Fischer et al. | 504/138 |
| 5,508,436 | 4/1996 | Fischer et al. | 548/544 |

FOREIGN PATENT DOCUMENTS

| | | |
|---|---|---|
| 442073 | 12/1990 | European Pat. Off. . |
| 456063 | 4/1991 | European Pat. Off. . |
| 501129 | 1/1992 | European Pat. Off. . |
| 521334 | 6/1992 | European Pat. Off. . |

OTHER PUBLICATIONS

Fischer et al., Chemical Abstracts 119(1):8676w, Jul. 5, 1993 Abstract of EP 521334.

Krauskopf et al., Chemical Abstracts 116(11) 106083h, May 16, 1992 Abstract of EP 456,063.

Chemical Abstracts, vol. 53, Aug. 25, 1959, No. 16, "1–Apparatus, Plant Equipment, and Operations".

*Primary Examiner*—Matthew V. Grumbling
*Attorney, Agent, or Firm*—Sprung Kramer Schaefer & Briscoe

[57] ABSTRACT

The invention relates to new 1-H-3-aryl-pyrrolidine-2,4-dione derivatives of the formula (I)

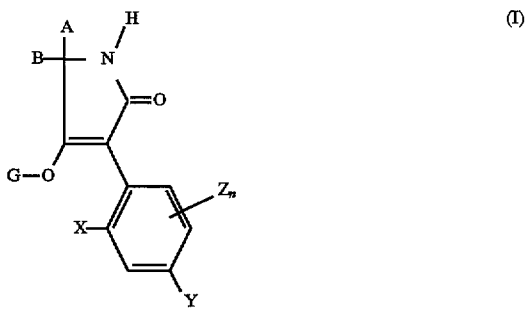

in which

A and B together with the carbon atom to which they are bonded represent a substituted cycle, X represents alkyl, halogen or alkoxy, Y represents hydrogen, alkyl, halogen, alkoxy or halogenoalkyl, Z represents alkyl, halogen or alkoxy, n represents 0, 1, 2 or 3, G is defined in the claims, to processes for their preparation, and to their use as pesticides.

4 Claims, No Drawings

SUBSTITUTED 1-H-3-ARYL-PYRROLIDINE-2,4-DIONE DERIVATIVES

This is a division of application Ser. No. 08/140,635, filed on Oct. 21, 1993, now U.S. Pat. No. 5,462,913.

The invention relates to 1-H-3-aryl-pyrrolidine-2,4-dione derivatives, to a plurality of processes for their preparation and to their use as pesticides (in particular as insecticides and acaricides) and as herbicides.

It has previously been described that 3-acyl-pyrrolidine-2,4-diones have pharmaceutical properties (S. Suzuki et al. Chem. Pharm. Bull 15 1120 (1967)). N-Phenyl-pyrrolidine-2,4-diones were furthermore synthesized by R. Schmierer and H. Mildenberger (Liebigs Ann. Chem. 1985 1095). A biological activity of these compounds has not been described.

EP-A 0,262,399 discloses compounds which have a similar structure (3-aryl-pyrrolidine-2,4-diones), but nothing has been disclosed about them as having a herbicidal, insecticidal or acaricidal activity. Unsubstitutedt bicyclic 3-aryl-pyrrolidine-2,4-dione derivatives (EP-A 355 599) and (EP 415,211) as well as substituted monocyclic 3-aryl-pyrrolidine-2,4-dione derivatives (EP-A377,893, EP 442, 077, and EP 497 127)have been disclosed and have a herbicidal, insecticidal or acaricidal activity.

Polycyclic 3-arylpyrrolidine-2,4-dione derivatives (EP 442 073), substituted bicyclic 3-arylpyrrolidine-2,4-diones as well as 1-H-3-arylpyrrolidine-dione derivatives (EP 456 063, EP 521 334, EP 501 129) have also been disclosed.

New substituted spirocyclic 1-H-3-aryl-pyrolidine-2,4-dione derivatives of the formula (I)

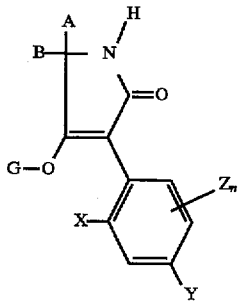

have now been found, in which

A and B together with the carbon atom to which they are bonded represent a substituted cycle, X represents alkyl, halogen or alkoxy, Y represents hydrogen, alkyl, halogen, alkoxy or halogenoalkyl, Z represents alkyl, halogen or alkoxy, n represents 0, 1, 2 or 3, G represents hydrogen (a) or the groups

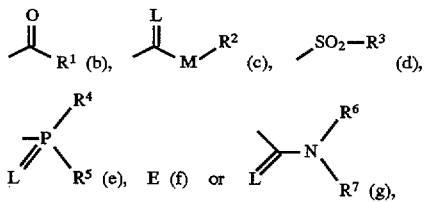

E represents a metal ion equivalent or an ammonium ion,

L and M represent oxygen and/or sulphur, $R^1$ represents in each case optionally halogen-substituted alkyl, alkenyl, alkoxyalkyl, alkylthioalkyl, polyalkoxyalkyl or cycloalkyl, which can be interrupted by hetero atoms, optionally substituted phenyl, optionally substituted phenylalkyl, substituted hetaryl, substituted phenoxyalkyl or substituted hetaryloxyalkyl, $R^2$ represents in each case optionally halogen-substituted alkyl alkenyl, alkoxyalkyl, polyalkoxyalkyl or in each case optionally substituted phenyl or benzyl, $R^3$, $R^4$ and $R^5$ independently of one another represent in each case optionally halogen-substituted alkyl, alkoxy, alkylamino, dialkyamino, alkylthio, alkenylthio, cycloalkylthio and in each case optionally substituted phenyl, phenoxy or phenylthio, $R^6$ and $R^7$ independently of one another represent hydrogen, in each case optionally halogen-substituted alkyl, alkenyl, alkoxy, alkoxyalkyl, or represent optionally substituted phenyl, optionally substituted benzyl, or, together with the adjacent N-atom, represent a cycle which is optionally interrupted by oxygen or sulphur.

Taking into account the various meanings (a), (b), (c), (d), (e), and (f) of group G of the general formula (I), the following main structures (Ia) to (Ig) result:

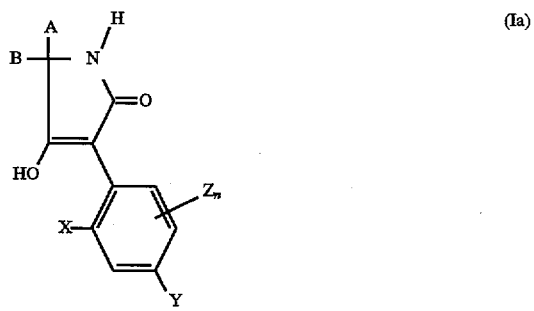

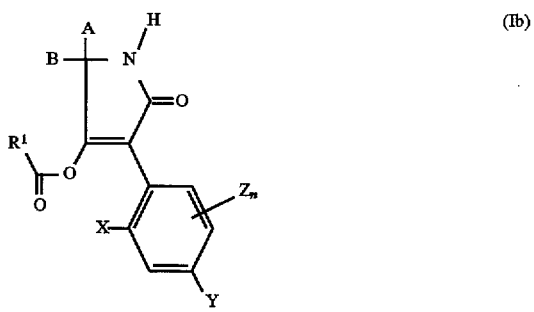

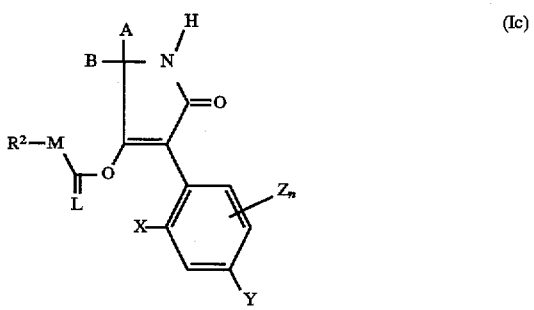

-continued

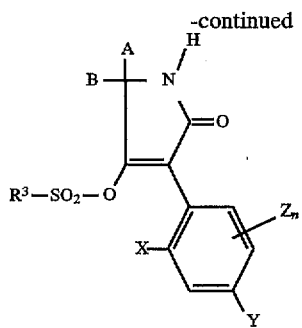
(Id)

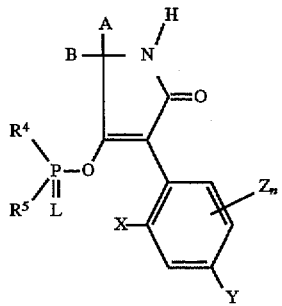
(Ie)

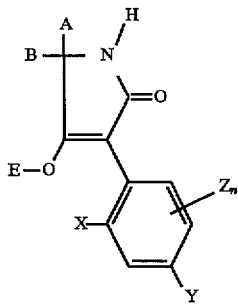
(If)

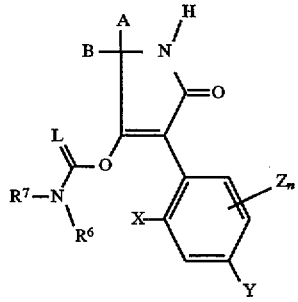
(Ig)

in which
A, B, E, L, M, X, Y, Z, $R^1$, $R^2$, $R^3$, $R^4$, $R^5$, $R^6$, $R^7$ and n have the abovementioned meanings.

Due to one or more chiral centres, the compounds of the formula (Ia)–(Ig) are generally obtained in the form of a stereoisomer mixture which can be resolved, if appropriate, in the customary manner. They can be used in the form of their diasteromer mixtures as well as in the form of pure diasteromers or enantiomers. The text hereinafter will always discuss compounds of the formula (Ia) to (Ig), for the sake of simplicity, even though this is to be understood as meaning the pure compounds as well as the mixtures which contain various proportions of isomeric, enantiomeric and stereomeric compounds.

Furthermore, it has been found that the new substituted 1-H-3-aryl-pyrrolidine-2,4-dione derivatives of the formula (I) are obtained by one of the processes described below.

(A) 1-H-3-Aryl-pyrrolidine-2,4-diones or their enols of the formula (Ia)

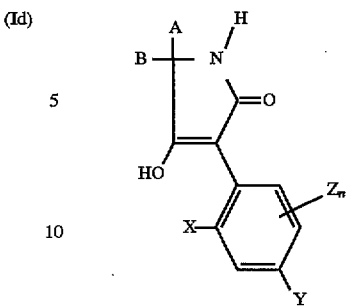
(Ia)

in which
A, B, X, Y, Z and n have the abovementioned meaning, are obtained when
N-acylamino acid esters of the formula (II)

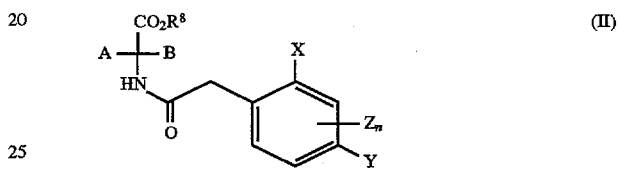
(II)

in which
A, B, X, Y, Z and n have the abovementioned meaning and
$R^8$ represents alkyl
are subjected to an intramolecular condensation reaction in the presence of a diluent and in the presence of a base; or
(B) compounds of the formula (Ib)

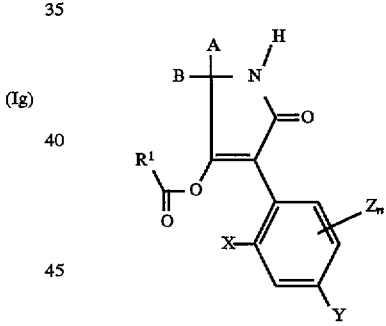
(Ib)

in which
A, B, X, Y, Z, $R^1$ and n have the abovementioned meaning are obtained when compounds of the formula (Ia)

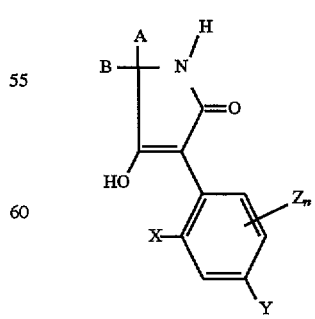
(Ia)

in which
A, B, X, Y, Z and n have the abovementioned meaning (α) are reacted with acid halides of the general formula (III)

 (III)

in which

R¹ has the abovementioned meaning and

Hal represents halogen, in particular chlorine and bromine, if appropriate in the presence of a diluent and if appropriate in the presence of an acid-binding agent, or (β) are reacted with carboxylic anhydrides of the general formula (IV)

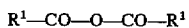 (IV)

in which

R¹ has the abovementioned meaning, if appropriate in the presence of a diluent and if appropriate in the presence of an acid-binding agent;

or (C) compounds of the formula (Ic-1)

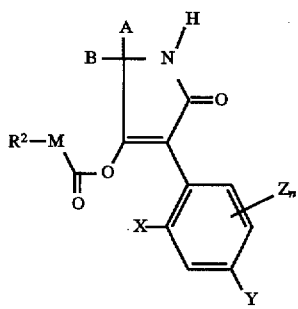 (Ic-1)

in which

A, B, X, Y, Z, R² and n have the abovementioned meaning and

M represents oxygen or sulphur are obtained when compounds of the formula (Ia)

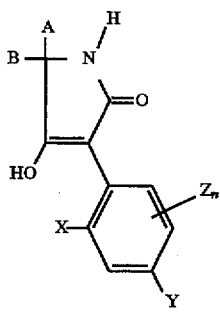 (Ia)

in which

A, B, X, Y, Z and n have the abovementioned meaning, are reacted with chloroformic ester or chloroformic thioester of the general formula (V)

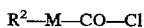 (V)

in which

R² and M have the abovementioned meaning, if appropriate in the presence of a diluent and if appropriate in the presence of an acid-binding agent;

or (D) compounds of the formula (Ic-2)

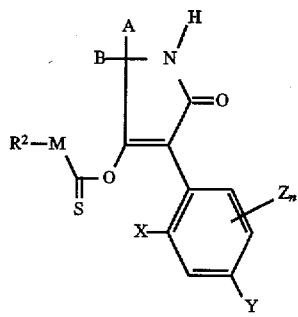 (Ic-2)

in which

A, B, R², X, Y, Z and n have the abovementioned meaning and

M represents oxygen or sulphur are obtained when compounds of the formula (Ia)

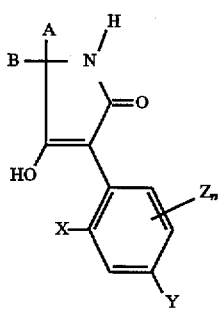 (Ia)

in which

A, B, X, Y, Z and n have the abovementioned meaning

α) are reacted with chloromonothioformic esters or chlorodithioformic esters of the general formula (VI)

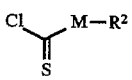 (VI)

in which

M and R² have the abovementioned meaning, if appropriate in the presence of a diluent and if appropriate in the presence of a acid-binding agent, or β) are reacted with carbon disulphide and subsequently with alkyl halides of the general formula (VII)

 (VII)

in which

R² has the abovementioned meaning and

Hal represents chlorine, bromine or iodine; optionally in the presence of a diluent or an acid binding agent or (E) compounds of the formula (Id)

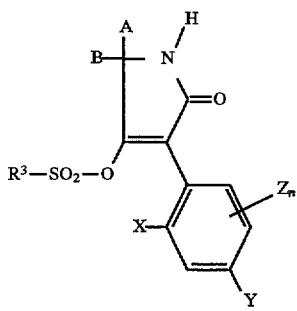

in which

A, B, X, Y, Z, $R^3$ and n have the abovementioned meaning are obtained when compounds of the formula (Ia)

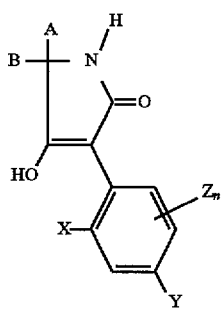

in which

A, B, X, Y, Z and n have the abovementioned meaning are reacted with sulphonyl chlorides of the general formula (VII)

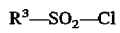

in which $R^3$ has the abovementioned meaning, if appropriate in the presence of a diluent and if appropriate in the presence of an acid-binding agent;

or (F) compounds of the formula (Ie)

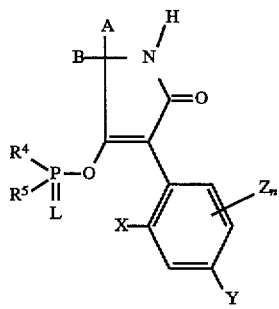

in which

A, B, L, X, Y, Z, $R^4$, $R^5$ and n have the abovementioned meaning are obtained when 1-H-3-aryl-pyrrolidine-2,4-diones of the formula (Ia) or their enoles

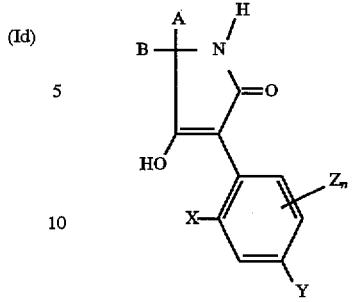

in which

A, B, X, Y, Z and n have the abovementioned meaning are reacted with phosphorus compounds of the general formula (IX)

in which

L, $R^4$ and $R^5$ have the abovementioned meaning and

Hal represents halogen, in particular chlorine and bromine;

optionally in the presence of a diluent or an acid binding agent or (G) compounds of the formula (If)

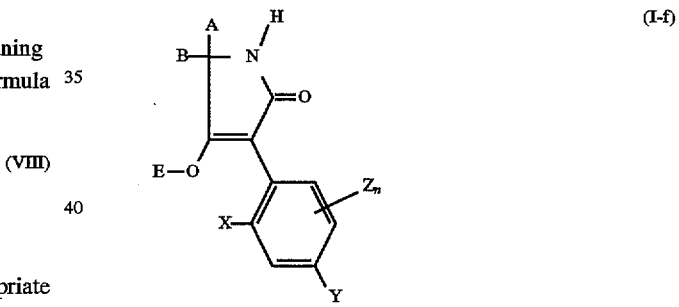

in which

A, B, X, Y, Z and n have the abovementioned meaning and

E represents a metal ion equivalent or an ammonium ion are obtained when compounds of the formula (Ia)

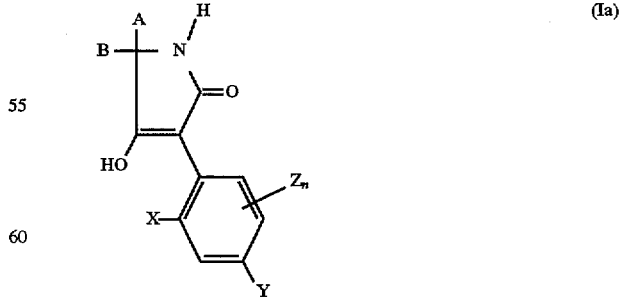

in which

A, B, X, Y, Z and n have the abovementioned meaning are reacted with metal hydroxides or amines of the general formula (X) and (XI)

$Me_sOH_t$ (X)

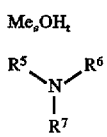
(XI)

in which

Me represents mono- or divalent metal ions, s and t represent the number 1 and 2 and $R^5$, $R^6$ and $R^7$ independently of one another represent hydrogen and alkyl, if appropriate in the presence of a diluent.

(H) Furthermore, it has been found that compounds of the formula (g)

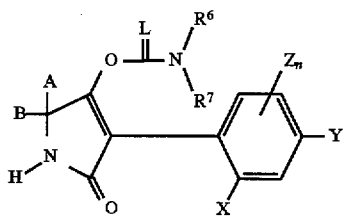
(Ig)

in which

A, B, L, X, Y, Z, $R^6$, $R^7$ and n have the above-mentioned meaning are obtained when compounds of the formula (Ia)

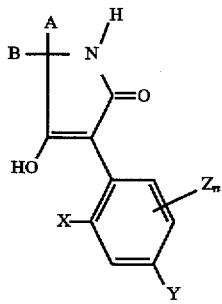
(Ia)

in which

A, B, X, Y, Z and n have the abovementioned meaning,

α) are reacted with compounds of the general formula (XII)

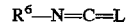
$R^6$—N=C=L (XII)

in which

L and $R^6$ have the abovementioned meaning, if appropriate in the presence of a diluent and if appropriate in the presence of a catalyst, or β) are reacted with carbamoyl chlorides or thiocarbamoyl chlorides of the general formula (XIII)

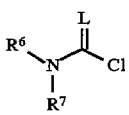
(XIII)

in which

L, $R^6$ and $R^7$ have the abovementioned meaning, if appropriate in the presence of a diluent and if appropriate in the presence of an acid-binding agent.

Furthermore, it has been found that the new 1-H-3-aryl-pyrrolidine-2,4-dione derivatives of the formula (I) are distinguished by outstanding insecticidal, acaricidal and herbicidal activities.

The following applies to the general formulae of the present application:

A, B and the carbon atom to which they are bonded preferably represent a $C_3$–$C_6$-spirocycle which can be monosubstituted or polysubstituted by alkyl, cycloalkyl, haloalkyl, alkoxy, thioalky, halogen or phenyl, or A, B and the carbon atom to which they are bonded preferably represent a $C_3$–$C_6$-spirocycle which is substituted by an alkylenediyl group which is optionally interrupted by one or two oxygen and/or sulphur atoms or by an alkylenedioxyl or an alkylenedithioyl group, which group, together with the carbon atom to which it is bonded, forms a further five- to eight-membered spirocycle, or A,B and the carbon atom to which they are bonded preferably represent a $C_3$–$C_6$-spirocycle in which two substituents together with the C-atoms to which they are bonded represent a saturated or unsaturated carbocycle which is optionally substituted by alkyl, alkoxy or halogen and which is optionally interrupted by oxygen or sulphur atom.

A, B and the carbon atom to which they are bonded particularly preferably represent a $C_3$–$C_6$-spirocycle which can be monosubstituted or polysubstituted by $C_1$–$C_6$-alkyl, $C_3$–$C_8$-cycloalkyl, $C_1$–$C_3$-haloalkyl, $C_1$–$C_4$-alkoxy, $C_1$–$C_4$-thioalkyl, fluorine, chlorine or phenyl, or A, B and the carbon atom to which they are bonded particularly preferably represent a $C_3$–$C_6$-spirocycle which is substituted by an alkylenediyl group which is optionally interrupted by one or two oxygen or sulphur atoms or by an alkylenedioxyl or an alkylenedithiooxyl group which, together with the carbon atom to which it is bonded, forms a further five- to seven-membered spirocycle, or A, B and the carbon atom to which they are bonded particularly preferably represent a $C_3$–$C_6$-spirocycle in which two substituents together with the C-atoms to which they are bonded represent a saturated or unsaturated carbocyle which is substituted by alkyl($C_1$–$C_3$), alkoxy ($C_1$–$C_3$), or fluorine, chlorine or bromine and which is optionally interrupted by oxygen or sulphur atom.

A, B and the carbon atom to which they are bonded very particularly preferably represent a $C_3$–$C_6$-spirocycle which can be at least monosubstituted or polysubstituted by methyl, ethyl, propyl, isopropyl, butyl, iso-butyl, sec.-butyl, tert,-butyl, cyclo-hexyl, trifluoromethyl, methoxy, ethoxy, propoxy, isopropoxy, butoxy, isobutoxy, sec-butoxy, tert-butoxy, methylthio, fluorine, chlorine or phenyl or A, B and the carbon atom to which they are bonded very particularly preferably represent a $C_3$–$C_6$-spirocycle which is substituted by an alkylenediyl group which is optionally interrupted by an oxygen or sulphur atom or by an alkylenedioxyl group, which group, together with the carbon atom to which it is bonded, forms a further five- to seven-membered spirocycle, A, B and the carbon atom to which they are bonded very particularly preferably represent a $C_3$–$C_6$-spirocycle in which two substituents together with the carbon atoms to which they are bonded represent a saturated or unsaturated five- or six-membered cycle, which is optionally interrupted by oxygen or sulphur.

X preferably represents $C_1$–$C_6$-alkyl, halogen or $C_1$–$C_6$-alkoxy.

X particularly preferably represents $C_1$–$C_4$-alkyl, halogen or $C_1$–$C_4$-alkoxy.

X very particularly preferably represents methyl, ethyl, propyl, 2-propyl, fluorine, chlorine, bromine, methoxy or ethoxy.

Y preferably represents hydrogen, $C_1$–$C_6$-alkyl, halogen, $C_1$–$C_6$-alkoxy or $C_1$–$C_3$-halogenoalkyl.

Y particularly preferably represents hydrogen, $C_1$–$C_4$-alkyl, halogen, $C_1$–$C_4$-alkoxy or $C_1$–$C_2$-halogenoalkyl.

Y very particularly preferably represents hydrogen, methyl, ethyl, propyl, i-propyl, butyl, i-butyl, tert.-butyl, fluorine, chlorine, bromine, methoxy, ethoxy or trifluoromethyl.

Z preferably represents $C_1$–$C_6$-alkyl, halogen or $C_1$–$C_6$-alkoxy.

Z particularly preferably represents $C_1$–$C_4$-alkyl, halogen or $C_1$–$C_4$-alkoxy.

Z very particularly preferably represents methyl, ethyl, propyl, i-propyl, butyl, i-butyl, tert.-butyl, fluorine, chlorine, bromine, methoxy or ethoxy.

n preferably means whole figures from 0 to 3.

n particularly preferably means 0, 1 or 2.

n very particularly preferably means 0 or 1.

G preferably represents hydrogen (a) or the groups

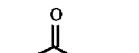 (b)

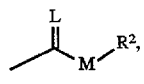 (c)

 (d)

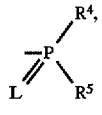 (e)

E (f)

or

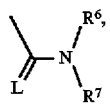 (g)

in which

E a metal ion equivalent or an ammonium ion and

L and M in each case represent oxygen and/or sulphur, $R^1$ represents in each case optionally halogen-substituted $C_1$–$C_{20}$-alkyl, $C_2$–$C_{20}$-alkenyl, $C_1$–$C_8$-alkoxy-$C_2$–$C_8$-alkyl, $C_1$–$C_8$-alkylthio-$C_2$–$C_8$-alkyl, $C_1$–$C_8$-polyalkoxy-$C_2$–$C_8$-alkyl or cycloalkyl which has 3 to 8 ring atoms and which can be interrupted by oxygen and/or sulphur atoms, or represents phenyl which is optionally substituted by halogen, nitro, $C_1$–$C_6$-alkyl, $C_1$–$C_6$-alkoxy, $C_1$–$C_6$-halogenoalkyl or $C_1$–$C_6$-halogenoalkoxy, or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which is optionally substituted by halogen and/or $C_1$–$C_6$-alkyl, or represents phenoxy-$C_1$–$C_6$-alkyl which is optionally substituted by halogen and $C_1$–$C_6$-alkyl, or represents hetaryloxy-$C_1$–$C_6$-alkyl which is optionally substituted by halogen, amino and $C_1$–$C_6$-alkyl, $R^2$ represents in each case optionally halogen-substituted $C_1$–$C_{20}$-alkyl, $C_3$–$C_{20}$-alkenyl, $C_1$–$C_8$-alkoxy-$C_2$–$C_8$-alkyl, $C_1$–$C_8$-polyalkoxy-$C_2$–$C_8$-alkyl, or represents phenyl or benzyl, in each case optionally substituted by halogen, nitro, $C_1$–$C_6$-alkyl, $C_1$–$C_6$-alkoxy or $C_1$–$C_6$-halogenoalkyl, $R^3$, $R^4$ and $R^5$ independently of one another represent in each case optionally halogen-substituted $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_3$-alkenylthio, $C_3$–$C_7$-cycloalkylthio, or represent phenyl, phenoxy or phenylthio, in each case optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halgenoalkylthio, $C_1$–$C_4$-alkyl or $C_1$–$C_4$-halogenoalkyl, $R^6$ and $R^7$ independently of one another represent hydrogen, or represent in each case optionally halogen-substituted $CV_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, or represent phenyl which is optionally substituted by halogen, $C_1$–$C_8$-halogenoalkyl, $C_1$–$C_8$-alkyl or $C_1$–$C_8$-alkoxy, or represent benzyl which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene ring which is optionally interrupted by oxygen or sulphur, G particularly preferably represents hydrogen (a) or the groups

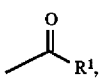 (b)

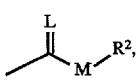 (c)

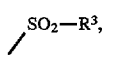 (d)

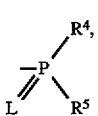 (e)

E (f)

or

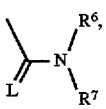 (g)

in which

E represents a metal ion equivalent or an ammonium ion,

L and M in each case represent oxygen and/or sulphur, $R^1$ represents in each case optionally halogen-substituted $C_1$–$C_{16}$-alkyl, $C_2$–$C_{16}$-alkenyl, $C_1$–$C_6$-alkoxy-$C_2$–$C_6$-alkyl, $C_1$–$C_{16}$-alkylthio-$C_2$–$C_6$-alkyl, $C_1$–$C_6$-polyalkoxy-$C_2$–$C_6$-alkyl or cycloalkyl which has 3 to 7 ring atoms and which can be interrupted by 1–2 oxygen and/or sulphur atoms, or represents phenyl which is optionally substituted by halogen, nitro, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, or represents hetaryl which is optionally substituted by fluorine, chlorine, bromine and/or $C_1$–$C_4$-alkyl, or represents phenoxy-$C_1$–$C_5$-alkyl which is optionally substituted by fluorine, chlorine, bromine and $C_1$–$C_4$-alkyl, or represents hetaryloxy-$C_1$–$C_5$-alkyl which is optionally substituted by fluorine, chlorine, bromine, amino and $C_1$–$C_4$-alkyl, $R^2$ represents in each case optionally halogen-substituted $C_1$–$C_{16}$-alkyl, $C_3$–$C_{16}$-alkenyl, $C_1$–$C_6$-alkoxy-$C_2$–$C_6$-alkyl, $C_1$–$C_6$-polyalkoxy-$C_2$–$C_6$-alkyl or, or represents phenyl or benzyl, in each case optionally substituted by halogen, nitro, $C_1$–$C_4$-alkyl, $C_1$–$C_3$-alkoxy or $C_1$–$C_3$-halogenoalkyl, $R^3$, $R^4$ and $R^5$ independently of one another represent in each case optionally halogen-substituted $C_1$–$C_6$-alkyl, $C_1$–$C_6$-alkoxy, $C_1$–$C_6$-alkylamino, di-,($C_1$–$C_6$)-alkylamino, $C_1$–$C_6$-alkylthio, $C_3$–$C_4$-alkenylthio, $C_3$–$C_6$-cycloalkylthio, or represent phenyl, phenoxy or phenylthio, in each case optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ and $R^7$ independently of one another represent hydrogen, or represent optionally halogen-substituted $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_2$–$C_6$-alkyl, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, or together represent a $C_3$–$C_6$-alkylene ring which is optionally substituted by oxygen or sulphur, G very particularly preferably represents hydrogen (a) or the groups

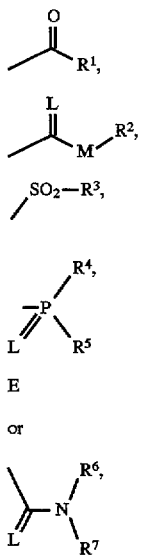

in which

E represents a metal ion equivalent or an ammonium ion and

L and M represent oxygen and/or sulphur, $R^1$ represents in each case optionally fluorine- or chlorine-substituted $C_1$–$C_{14}$-alkyl, $C_3$–$C_{14}$-alkenyl, $C_1$–$C_4$-alkoxy-$C_2$–$C_6$-alkyl, $C_1$–$C_4$-alkylthio-$C_2$–$C_6$-alkyl, $C_1$–$C_4$-polyalkoxy-$C_2$–$C_4$-alkyl or cycloalkyl which has 3 to 6 ring atoms and which can be interrupted by 1 to 2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy or nitro, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents furanoyl, pyridyl, pyrimidyl, thiazolyl and pyrazolyl, in each case optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl and thiazolyloxy-$C_1$–$C_4$-alkyl, in each case optionally substituted by fluorine, chlorine, amino, methyl or ethyl, $R^2$ represents in each case optionally fluorine- or chlorine substituted $C_1$–$C_{14}$-alkyl, $C_3$–$C_{14}$-alkenyl, $C_1$–$C_4$-alkoxy-$C_2$–$C_6$-alkyl or $C_1$–$C_4$-polyalkoxy-$C_2$–$C_6$-alkyl, or represents phenyl or benzyl, in each case optionally substituted by fluorine, chlorine, nitro, methyl, ethyl, propyl, i-propyl, methoxy, ethoxy or trifluoromethyl, $R^3$, $R^4$ and $R^5$ independently of one another represent $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, in each case optionally substituted by fluorine or chlorine, or represent phenyl, phenoxy or phenylthio, in each case optionally substituted by fluorine, chlorine, bromine, nitro, cyano, $C_1$–$C_2$-alkoxy, $C_1$–$C_4$-fluoroalkoxy, $C_1$–$C_2$-alkylthio, $C_1$–$C_2$-fluoroalkylthio or $C_1$–$C_3$-alkyl, $R^6$ and $R^7$ independently of one another represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, in each case optionally substituted by fluorine, chlorine or bromine, or represent phenyl which is optionally substituted by fluorine, chlorine, bromine, $C_1$–$C_4$-halogenoalkyl, $C_1$–$C_4$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_4$-alkoxy, or together represent a $C_4$–$C_6$-alkylene ring which is optionally substituted by oxygen or sulphur.

The following compounds of the formula (Ia) may be mentioned individually in addition to the compounds mentioned in the preparation examples:

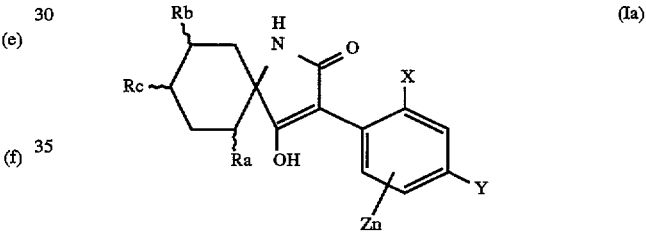

(Ia)

TABLE 1

| X | Y | $Z_n$ | $R_a$ | $R_b$ | $R_c$ |
|---|---|---|---|---|---|
| Cl | Cl | H | H | $CH_3$ | H |
| Cl | Cl | H | H | H | $CH_3$ |
| Cl | Cl | H | H | H | $C_2H_5$ |
| Cl | Cl | H | H | H | $i$-$C_3H_7$ |
| Cl | Cl | H | H | H | $t$-$C_4H_9$ |
| Cl | Cl | H | H | $CH_3$ | $CH_3$ |
| Cl | H | 6-F | $CH_3$ | H | H |
| Cl | H | 6-F | H | $CH_3$ | H |
| Cl | H | 6-F | H | H | $CH_3$ |
| Cl | H | 6-F | H | H | $C_2H_5$ |
| Cl | H | 6-F | H | H | $i$-$C_3H_7$ |
| Cl | H | 6-F | H | H | $t$-$C_4H_9$ |
| Cl | H | 6-F | H | $CH_3$ | $CH_3$ |
| Cl | H | 6-Cl | $CH_3$ | H | H |
| Cl | H | 6-Cl | H | $CH_3$ | H |
| Cl | H | 6-Cl | H | H | $CH_3$ |
| Cl | H | 6-Cl | H | H | $C_2H_5$ |
| Cl | H | 6-Cl | H | H | $i$-$C_3H_7$ |
| Cl | H | 6-Cl | H | H | $t$-$C_4H_9$ |
| Cl | H | 6-Cl | H | $CH_3$ | $CH_3$ |
| $CH_3$ | $CH_3$ | H | $CH_3$ | H | H |
| $CH_3$ | $CH_3$ | H | H | $CH_3$ | H |
| $CH_3$ | $CH_3$ | H | H | H | $CH_3$ |
| $CH_3$ | $CH_3$ | H | H | H | $C_2H_5$ |
| $CH_3$ | $CH_3$ | H | H | H | $i$-$C_3H_7$ |
| $CH_3$ | $CH_3$ | H | H | H | $i$-$C_4H_9$ |
| $CH_3$ | $CH_3$ | H | H | $CH_3$ | $CH_3$ |
| $CH_3$ | $CH_3$ | 6-$CH_3$ | H | $CH_3$ | H |
| $CH_3$ | $CH_3$ | 6-$CH_3$ | H | H | $C_2H_5$ |

TABLE 1-continued

| X | Y | $Z_n$ | $R_a$ | $R_b$ | $R_c$ |
|---|---|---|---|---|---|
| $CH_3$ | $CH_3$ | 6-$CH_3$ | H | H | i-$C_3H_7$ |
| $CH_3$ | $CH_3$ | 6-$CH_3$ | H | H | t-$C_4H_9$ |
| $CH_3$ | $CH_3$ | 6-$CH_3$ | H | $CH_3$ | $CH_3$ |

The following compounds of the formula (Ib) may be mentioned individually in addition to the compounds mentioned in the preparation examples:

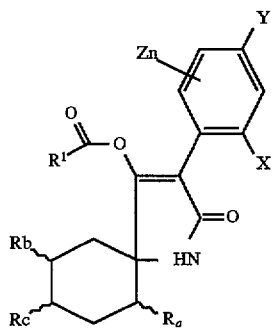

(Ib)

TABLE 2

| X | Y | $Z_n$ | $R_a$ | $R_b$ | $R_c$ | $R^1$ |
|---|---|---|---|---|---|---|
| Cl | Cl | H | $CH_3$ | H | H | $CH_3$ |
| Cl | Cl | H | H | $CH_3$ | H | $CH_3$ |
| Cl | Cl | H | H | H | $CH_3$ | $CH_3$ |
| Cl | Cl | H | H | H | $C_2H_5$ | $CH_3$ |
| Cl | Cl | H | H | H | i-$C_3H_7$ | $CH_3$ |
| Cl | Cl | H | H | H | t-$C_4H_9$ | $CH_3$ |
| Cl | Cl | H | H | $CH_3$ | $CH_3$ | $CH_3$ |
| Cl | H | 6-F | $CH_3$ | H | H | $CH_3$ |
| Cl | H | 6-F | H | $CH_3$ | H | $CH_3$ |
| Cl | H | 6-F | H | H | $CH_3$ | $CH_3$ |
| Cl | H | 6-F | H | H | $C_2H_5$ | $CH_3$ |
| Cl | H | 6-F | H | H | i-$C_3H_7$ | $CH_3$ |
| Cl | H | 6-F | H | H | t-$C_4H_9$ | $CH_3$ |
| Cl | H | 6-F | H | $CH_3$ | $CH_3$ | $CH_3$ |
| Cl | H | 6-Cl | $CH_3$ | H | H | $CH_3$ |
| Cl | H | 6-Cl | H | $CH_3$ | H | $CH_3$ |
| Cl | H | 6-Cl | H | H | $CH_3$ | $CH_3$ |
| Cl | H | 6-Cl | H | H | $C_2H_5$ | $CH_3$ |
| Cl | H | 6-Cl | H | H | i-$C_3H_7$ | $CH_3$ |
| Cl | H | 6-Cl | H | H | t-$C_4H_9$ | $CH_3$ |
| Cl | H | 6-Cl | H | $CH_3$ | $CH_3$ | $CH_3$ |
| $CH_3$ | $CH_3$ | H | $CH_3$ | H | H | $CH_3$ |
| $CH_3$ | $CH_3$ | H | H | $CH_3$ | H | $CH_3$ |
| $CH_3$ | $CH_3$ | H | H | H | $CH_3$ | $CH_3$ |
| $CH_3$ | $CH_3$ | H | H | H | $C_2H_5$ | $CH_3$ |
| $CH_3$ | $CH_3$ | H | H | H | i-$C_3H_7$ | $CH_3$ |
| $CH_3$ | $CH_3$ | H | H | H | t-$C_4H_9$ | $CH_3$ |
| $CH_3$ | $CH_3$ | H | H | $CH_3$ | $CH_3$ | $CH_3$ |
| $CH_3$ | $CH_3$ | 6-$CH_3$ | H | $CH_3$ | H | $CH_3$ |
| $CH_3$ | $CH_3$ | 6-$CH_3$ | $CH_3$ | $CH_3$ | H | $CH_3$ |
| $CH_3$ | $CH_3$ | 6-$CH_3$ | H | H | $C_2H_5$ | $CH_3$ |
| $CH_3$ | $CH_3$ | 6-$CH_3$ | H | H | i-$C_3H_7$ | $CH_3$ |
| $CH_3$ | $CH_3$ | 6-$CH_3$ | H | H | t-$C_4H_9$ | $CH_3$ |
| $CH_3$ | $CH_3$ | 6-$CH_3$ | H | $CH_3$ | $CH_3$ | $CH_3$ |
| Cl | Cl | H | $CH_3$ | H | H | i-$C_3H_7$ |
| Cl | Cl | H | H | $CH_3$ | H | i-$C_3H_7$ |
| Cl | Cl | H | H | H | $CH_3$ | i-$C_3H_7$ |
| Cl | Cl | H | H | H | $C_2H_5$ | i-$C_3H_7$ |
| Cl | Cl | H | H | H | i-$C_3H_7$ | i-$C_3H_7$ |
| Cl | Cl | H | H | H | t-$C_4H_9$ | i-$C_3H_7$ |
| Cl | Cl | H | H | $CH_3$ | $CH_3$ | i-$C_3H_7$ |
| Cl | H | 6-F | $CH_3$ | H | H | i-$C_3H_7$ |
| Cl | H | 6-F | H | $CH_3$ | H | i-$C_3H_7$ |
| Cl | H | 6-F | H | H | $CH_3$ | i-$C_3H_7$ |
| Cl | H | 6-F | H | H | $C_2H_5$ | i-$C_3H_7$ |

TABLE 2-continued

| X | Y | $Z_n$ | $R_a$ | $R_b$ | $R_c$ | $R^1$ |
|---|---|---|---|---|---|---|
| Cl | H | 6-F | H | H | i-$C_3H_7$ | i-$C_3H_7$ |
| Cl | H | 6-F | H | H | t-$C_4H_9$ | i-$C_3H_7$ |
| Cl | H | 6-F | H | $CH_3$ | $CH_3$ | i-$C_3H_7$ |
| Cl | H | 6-Cl | $CH_3$ | H | H | i-$C_3H_7$ |
| Cl | H | 6-Cl | H | $CH_3$ | H | i-$C_3H_7$ |
| Cl | H | 6-Cl | H | H | $CH_3$ | i-$C_3H_7$ |
| Cl | H | 6-Cl | H | H | $C_2H_5$ | i-$C_3H_7$ |
| Cl | H | 6-Cl | H | H | i-$C_3H_7$ | i-$C_3H_7$ |
| Cl | H | 6-Cl | H | H | t-$C_4H_9$ | i-$C_3H_7$ |
| Cl | H | 6-Cl | H | $CH_3$ | $CH_3$ | i-$C_3H_7$ |
| $CH_3$ | $CH_3$ | H | $CH_3$ | H | H | i-$C_3H_7$ |
| $CH_3$ | $CH_3$ | H | H | $CH_3$ | H | i-$C_3H_7$ |
| $CH_3$ | $CH_3$ | H | H | H | $CH_3$ | i-$C_3H_7$ |
| $CH_3$ | $CH_3$ | H | H | H | $C_2H_5$ | i-$C_3H_7$ |
| $CH_3$ | $CH_3$ | H | H | H | i-$C_3H_7$ | i-$C_3H_7$ |
| $CH_3$ | $CH_3$ | H | H | H | t-$C_4H_9$ | i-$C_3H_7$ |
| $CH_3$ | $CH_3$ | H | H | $CH_3$ | $CH_3$ | i-$C_3H_7$ |
| $CH_3$ | $CH_3$ | 6-$CH_3$ | $CH_3$ | H | H | i-$C_3H_7$ |
| $CH_3$ | $CH_3$ | 6-$CH_3$ | H | $CH_3$ | H | i-$C_3H_7$ |
| $CH_3$ | $CH_3$ | 6-$CH_3$ | H | H | $CH_3$ | i-$C_3H_7$ |
| $CH_3$ | $CH_3$ | 6-$CH_3$ | H | H | $C_2H_5$ | i-$C_3H_7$ |
| $CH_3$ | $CH_3$ | 6-$CH_3$ | H | H | i-$C_3H_7$ | i-$C_3H_7$ |
| $CH_3$ | $CH_3$ | 6-$CH_3$ | H | H | t-$C_4H_9$ | i-$C_3H_7$ |
| $CH_3$ | $CH_3$ | 6-$CH_3$ | H | $CH_3$ | $CH_3$ | i-$C_3H_7$ |
| Cl | Cl | H | $CH_3$ | H | H | t-$C_4H_9$ |
| Cl | Cl | H | H | $CH_3$ | H | t-$C_4H_9$ |
| Cl | Cl | H | H | H | $CH_3$ | t-$C_4H_9$ |
| Cl | Cl | H | H | H | $C_2H_5$ | t-$C_4H_9$ |
| Cl | Cl | H | H | H | i-$C_3H_7$ | t-$C_4H_9$ |
| Cl | Cl | H | H | H | t-$C_4H_9$ | t-$C_4H_9$ |
| Cl | Cl | H | H | $CH_3$ | $CH_3$ | t-$C_4H_9$ |
| Cl | H | 6-F | $CH_3$ | H | H | t-$C_4H_9$ |
| Cl | H | 6-F | H | $CH_3$ | H | t-$C_4H_9$ |
| Cl | H | 6-F | H | H | $CH_3$ | t-$C_4H_9$ |
| Cl | H | 6-F | H | H | $C_2H_5$ | t-$C_4H_9$ |
| Cl | H | 6-F | H | H | i-$C_3H_7$ | t-$C_4H_9$ |
| Cl | H | 6-F | H | H | t-$C_4H_9$ | t-$C_4H_9$ |
| Cl | H | 6-F | H | $CH_3$ | $CH_3$ | t-$C_4H_9$ |
| Cl | H | 6-Cl | $CH_3$ | H | H | t-$C_4H_9$ |
| Cl | H | 6-Cl | H | $CH_3$ | H | t-$C_4H_9$ |
| Cl | H | 6-Cl | H | H | $CH_3$ | t-$C_4H_9$ |
| Cl | H | 6-Cl | H | H | $C_2H_5$ | t-$C_4H_9$ |
| Cl | H | 6-Cl | H | H | i-$C_3H_7$ | t-$C_4H_9$ |
| Cl | H | 6-Cl | H | H | t-$C_4H_9$ | t-$C_4H_9$ |
| Cl | H | 6-Cl | H | $CH_3$ | $CH_3$ | t-$C_4H_9$ |
| $CH_3$ | $CH_3$ | H | $CH_3$ | H | H | t-$C_4H_9$ |
| $CH_3$ | $CH_3$ | H | H | $CH_3$ | H | t-$C_4H_9$ |
| $CH_3$ | $CH_3$ | H | H | H | $CH_3$ | t-$C_4H_9$ |
| $CH_3$ | $CH_3$ | H | H | H | $C_2H_5$ | t-$C_4H_9$ |
| $CH_3$ | $CH_3$ | H | H | H | i-$C_3H_7$ | t-$C_4H_9$ |
| $CH_3$ | $CH_3$ | H | H | H | t-$C_4H_9$ | t-$C_4H_9$ |
| $CH_3$ | $CH_3$ | H | H | $CH_3$ | $CH_3$ | t-$C_4H_9$ |
| $CH_3$ | $CH_3$ | 6-$CH_3$ | $CH_3$ | H | H | t-$C_4H_9$ |
| $CH_3$ | $CH_3$ | 6-$CH_3$ | H | $CH_3$ | H | t-$C_4H_9$ |
| $CH_3$ | $CH_3$ | 6-$CH_3$ | H | H | $CH_3$ | t-$C_4H_9$ |
| $CH_3$ | $CH_3$ | 6-$CH_3$ | H | H | $C_2H_5$ | t-$C_4H_9$ |
| $CH_3$ | $CH_3$ | 6-$CH_3$ | H | H | i-$C_3H_7$ | t-$C_4H_9$ |
| $CH_3$ | $CH_3$ | 6-$CH_3$ | H | H | t-$C_4H_9$ | t-$C_4H_9$ |
| $CH_3$ | $CH_3$ | 6-$CH_3$ | H | $CH_3$ | $CH_3$ | t-$C_4H_9$ |
| Cl | Cl | H | $CH_3$ | H | H | —C₆H₄—Cl |
| Cl | Cl | H | H | $CH_3$ | H | —C₆H₄—Cl |
| Cl | Cl | H | H | H | $CH_3$ | —C₆H₄—Cl |

TABLE 2-continued

| X | Y | $Z_n$ | $R_a$ | $R_b$ | $R_c$ | $R^1$ |
|---|---|---|---|---|---|---|
| Cl | Cl | H | H | H | $C_2H_5$ | 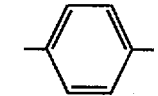—C₆H₄—Cl |
| Cl | Cl | H | H | H | $i\text{-}C_3H_7$ | 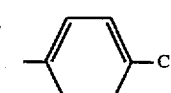—C₆H₄—Cl |
| Cl | Cl | H | H | H | $t\text{-}C_4H_9$ | 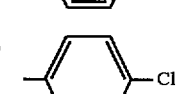—C₆H₄—Cl |
| Cl | Cl | H | H | $CH_3$ | $CH_3$ | 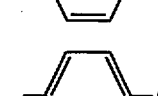—C₆H₄—Cl |
| Cl | H | 6-F | $CH_3$ | H | H | 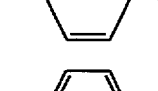—C₆H₄—Cl |
| Cl | H | 6-F | H | $CH_3$ | H | 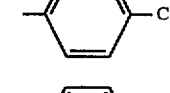—C₆H₄—Cl |
| Cl | H | 6-F | H | H | $CH_3$ | 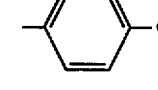—C₆H₄—Cl |
| Cl | H | 6-F | H | H | $C_2H_5$ | 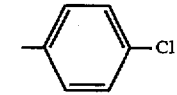—C₆H₄—Cl |
| Cl | H | 6-F | H | H | $i\text{-}C_3H_7$ | 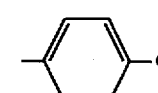—C₆H₄—Cl |
| Cl | H | 6-F | H | H | $t\text{-}C_4H_9$ | 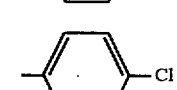—C₆H₄—Cl |
| Cl | H | 6-F | H | $CH_3$ | $CH_3$ | —C₆H₄—Cl |
| Cl | H | 6-Cl | $CH_3$ | H | H | 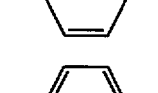—C₆H₄—Cl |
| Cl | H | 6-Cl | H | $CH_3$ | H | 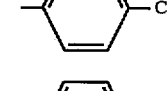—C₆H₄—Cl |
| Cl | H | 6-Cl | H | H | $CH_3$ | 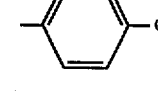—C₆H₄—Cl |
| Cl | H | 6-Cl | H | H | $C_2H_5$ | —C₆H₄—Cl |
| Cl | H | 6-Cl | H | H | $i\text{-}C_3H_7$ | —C₆H₄—Cl |
| Cl | H | 6-Cl | H | H | $t\text{-}C_4H_9$ | 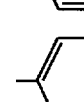—C₆H₄—Cl |
| Cl | H | 6-Cl | H | $CH_3$ | $CH_3$ | —C₆H₄—Cl |
| $CH_3$ | $CH_3$ | H | $CH_3$ | H | H | —C₆H₄—Cl |
| $CH_3$ | $CH_3$ | H | H | $CH_3$ | H | 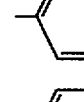—C₆H₄—Cl |
| $CH_3$ | $CH_3$ | H | H | H | $CH_3$ | —C₆H₄—Cl |
| $CH_3$ | $CH_3$ | H | H | H | $C_2H_5$ | —C₆H₄—Cl |
| $CH_3$ | $CH_3$ | H | H | H | $i\text{-}C_3H_7$ | 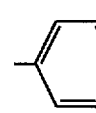—C₆H₄—Cl |
| $CH_3$ | $CH_3$ | H | H | H | $t\text{-}C_4H_9$ | —C₆H₄—Cl |
| $CH_3$ | $CH_3$ | H | H | $CH_3$ | $CH_3$ | —C₆H₄—Cl |
| $CH_3$ | $CH_3$ | 6-$CH_3$ | $CH_3$ | H | H | 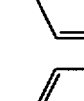—C₆H₄—Cl |
| $CH_3$ | $CH_3$ | 6-$CH_3$ | H | $CH_3$ | H | 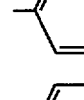—C₆H₄—Cl |

TABLE 2-continued

| X | Y | $Z_n$ | $R_a$ | $R_b$ | $R_c$ | $R^1$ |
|---|---|---|---|---|---|---|
| $CH_3$ | $CH_3$ | 6-$CH_3$ | H | H | $C_2H_5$ | 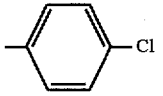 |
| $CH_3$ | $CH_3$ | 6-$CH_3$ | H | H | i-$C_3H_7$ | 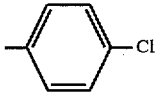 |
| $CH_3$ | $CH_3$ | 6-$CH_3$ | H | H | t-$C_4H_9$ | 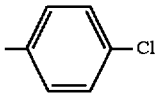 |
| $CH_3$ | $CH_3$ | 6-$CH_3$ | H | H | $CH_3$ | 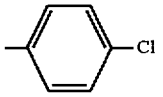 |

The following compounds of the formula (Ic) may be mentioned individually in addition to the compounds mentioned in the preparation examples:

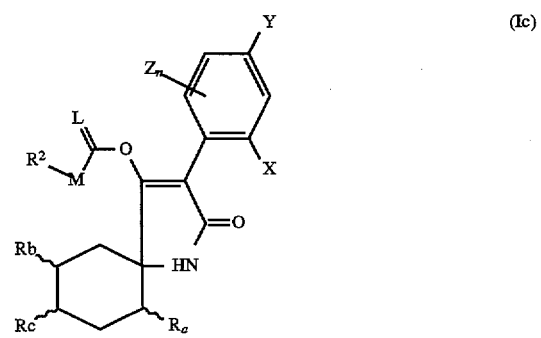

(Ic)

TABLE 3

| X | Y | $Z_n$ | $R_a$ | $R_b$ | $R_c$ | L | M | $R^2$ |
|---|---|---|---|---|---|---|---|---|
| Cl | Cl | H | $CH_3$ | H | H | O | O | $C_2H_5$ |
| Cl | Cl | H | H | $CH_3$ | H | O | O | $C_2H_5$ |
| Cl | Cl | H | H | H | $CH_3$ | O | O | $C_2H_5$ |
| Cl | Cl | H | H | H | $C_2H_5$ | O | O | $C_2H_5$ |
| Cl | Cl | H | H | H | i-$C_3H_7$ | O | O | $C_2H_5$ |
| Cl | Cl | H | H | H | t-$C_4H_9$ | O | O | $C_2H_5$ |
| Cl | Cl | H | H | $CH_3$ | $CH_3$ | O | O | $C_2H_5$ |
| Cl | H | 6-F | $CH_3$ | H | H | O | O | $C_2H_5$ |
| Cl | H | 6-F | H | $CH_3$ | H | O | O | $C_2H_5$ |
| Cl | H | 6-F | H | H | $CH_3$ | O | O | $C_2H_5$ |
| Cl | H | 6-F | H | H | $C_2H_5$ | O | O | $C_2H_5$ |
| Cl | H | 6-F | H | H | i-$C_3F_7$ | O | O | $C_2H_5$ |
| Cl | H | 6-F | H | H | t-$C_4H_9$ | O | O | $C_2H_5$ |
| Cl | H | 6-F | H | $CH_3$ | $CH_3$ | O | O | $C_2H_5$ |
| Cl | H | 6-Cl | $CH_3$ | H | H | O | O | $C_2H_5$ |
| Cl | H | 6-Cl | H | $CH_3$ | H | O | O | $C_2H_5$ |
| Cl | H | 6-Cl | H | H | $CH_3$ | O | O | $C_2H_5$ |
| Cl | H | 6-Cl | H | H | $C_2H_5$ | O | O | $C_2H_5$ |
| Cl | H | 6-Cl | H | H | i-$C_3H_7$ | O | O | $C_2H_5$ |
| Cl | H | 6-Cl | H | H | t-$C_4H_9$ | O | O | $C_2H_5$ |
| Cl | H | 6-Cl | H | $CH_3$ | $CH_3$ | O | O | $C_2H_5$ |
| $CH_3$ | $CH_3$ | H | $CH_3$ | H | H | O | O | $C_2H_5$ |
| $CH_3$ | $CH_3$ | H | H | $CH_3$ | H | O | O | $C_2H_5$ |
| $CH_3$ | $CH_3$ | H | H | H | $CH_3$ | O | O | $C_2H_5$ |
| $CH_3$ | $CH_3$ | H | H | H | $C_2H_5$ | O | O | $C_2H_5$ |
| $CH_3$ | $CH_3$ | H | H | H | i-$C_3H_7$ | O | O | $C_2H_5$ |
| $CH_3$ | $CH_3$ | H | H | H | t-$C_4H_9$ | O | O | $C_2H_5$ |
| $CH_3$ | $CH_3$ | H | H | $CH_3$ | $CH_3$ | O | O | $C_2H_5$ |
| $CH_3$ | $CH_3$ | 6-$CH_3$ | $CH_3$ | H | H | O | O | $C_2H_5$ |
| $CH_3$ | $CH_3$ | 6-$CH_3$ | H | $CH_3$ | H | O | O | $C_2H_5$ |
| $CH_3$ | $CH_3$ | 6-$CH_3$ | H | H | $CH_3$ | O | O | $C_2H_5$ |
| $CH_3$ | $CH_3$ | 6-$CH_3$ | H | H | $C_2H_5$ | O | O | $C_2H_5$ |
| $CH_3$ | $CH_3$ | 6-$CH_3$ | H | H | i-$C_3H_7$ | O | O | $C_2H_5$ |
| $CH_3$ | $CH_3$ | 6-$CH_3$ | H | H | t-$C_4H_9$ | O | O | $C_2H_5$ |
| $CH_3$ | $CH_3$ | 6-$CH_3$ | H | H | $CH_3$ | O | O | $C_2H_5$ |
| Cl | Cl | H | $CH_3$ | H | H | O | O | i-$C_3H_7$ |
| Cl | Cl | H | H | $CH_3$ | H | O | O | i-$C_3H_7$ |
| Cl | Cl | H | H | H | $CH_3$ | O | O | i-$C_3H_7$ |
| Cl | Cl | H | H | H | $C_2H_5$ | O | O | i-$C_3H_7$ |
| Cl | Cl | H | H | H | i-$C_3H_7$ | O | O | i-$C_3H_7$ |
| Cl | Cl | H | H | H | t-$C_4H_9$ | O | O | i-$C_3H_7$ |
| Cl | Cl | H | H | $CH_3$ | $CH_3$ | O | O | i-$C_3H_7$ |
| Cl | H | 6-F | $CH_3$ | H | H | O | O | i-$C_3H_7$ |

TABLE 3-continued

| X | Y | $Z_n$ | $R_a$ | $R_b$ | $R_c$ | L | M | $R^2$ |
|---|---|---|---|---|---|---|---|---|
| Cl | H | 6-F | H | $CH_3$ | H | O | O | $i$-$C_3H_7$ |
| Cl | H | 6-F | H | H | $CH_3$ | O | O | $i$-$C_3H_7$ |
| Cl | H | 6-F | H | H | $C_2H_5$ | O | O | $i$-$C_3H_7$ |
| Cl | H | 6-F | H | H | $i$-$C_3H_7$ | O | O | $i$-$C_3H_7$ |
| Cl | H | 6-F | H | H | $t$-$C_4H_9$ | O | O | $i$-$C_3H_7$ |
| Cl | H | 6-F | H | $CH_3$ | $CH_3$ | O | O | $i$-$C_3H_7$ |
| Cl | H | 6-Cl | $CH_3$ | H | H | O | O | $i$-$C_3H_7$ |
| Cl | H | 6-Cl | H | $CH_3$ | H | O | O | $i$-$C_3H_7$ |
| Cl | H | 6-Cl | H | H | $CH_3$ | O | O | $i$-$C_3H_7$ |
| Cl | H | 6-Cl | H | H | $C_2H_5$ | O | O | $i$-$C_3H_7$ |
| Cl | H | 6-Cl | H | H | $i$-$C_3H_7$ | O | O | $i$-$C_3H_7$ |
| Cl | H | 6-Cl | H | H | $t$-$C_4H_9$ | O | O | $i$-$C_3H_7$ |
| Cl | H | 6-Cl | H | $CH_3$ | $CH_3$ | O | O | $i$-$C_3H_7$ |
| $CH_3$ | $CH_3$ | H | $CH_3$ | H | H | O | O | $i$-$C_3H_7$ |
| $CH_3$ | $CH_3$ | H | H | $CH_3$ | H | O | O | $i$-$C_3H_7$ |
| $CH_3$ | $CH_3$ | H | H | H | $CH_3$ | O | O | $i$-$C_3H_7$ |
| $CH_3$ | $CH_3$ | H | H | H | $C_2H_5$ | O | O | $i$-$C_3H_7$ |
| $CH_3$ | $CH_3$ | H | H | H | $i$-$C_3H_7$ | O | O | $i$-$C_3H_7$ |
| $CH_3$ | $CH_3$ | H | H | H | $t$-$C_4H_9$ | O | O | $i$-$C_3H_7$ |
| $CH_3$ | $CH_3$ | H | H | $CH_3$ | $CH_3$ | O | O | $i$-$C_3H_7$ |
| $CH_3$ | $CH_3$ | 6-$CH_3$ | $CH_3$ | H | H | O | O | $i$-$C_3H_7$ |
| $CH_3$ | $CH_3$ | 6-$CH_3$ | H | $CH_3$ | H | O | O | $i$-$C_3H_7$ |
| $CH_3$ | $CH_3$ | 6-$CH_3$ | H | H | $CH_3$ | O | O | $i$-$C_3H_7$ |
| $CH_3$ | $CH_3$ | 6-$CH_3$ | H | H | $C_2H_5$ | O | O | $i$-$C_3H_7$ |
| $CH_3$ | $CH_3$ | 6-$CH_3$ | H | H | $i$-$C_3H_7$ | O | O | $i$-$C_3H_7$ |
| $CH_3$ | $CH_3$ | 6-$CH_3$ | H | H | $t$-$C_4H_9$ | O | O | $i$-$C_3H_7$ |
| $CH_3$ | $CH_3$ | 6-$CH_3$ | H | H | $CH_3$ | O | O | $i$-$C_3H_7$ |
| Cl | Cl | H | $CH_3$ | H | H | O | O | $s$-$C_4H_9$ |
| Cl | Cl | H | H | $CH_3$ | H | O | O | $s$-$C_4H_9$ |
| Cl | Cl | H | H | H | $CH_3$ | O | O | $s$-$C_4H_9$ |
| Cl | Cl | H | H | H | $C_2H_5$ | O | O | $s$-$C_4H_9$ |
| Cl | Cl | H | H | H | $i$-$C_3H_7$ | O | O | $s$-$C_4H_9$ |
| Cl | Cl | H | H | H | $t$-$C_4H_9$ | O | O | $s$-$C_4H_9$ |
| Cl | Cl | H | H | $CH_3$ | $CH_3$ | O | O | $s$-$C_4H_9$ |
| Cl | H | 6-F | $CH_3$ | H | H | O | O | $s$-$C_4H_9$ |
| Cl | H | 6-F | H | $CH_3$ | H | O | O | $s$-$C_4H_9$ |
| Cl | H | 6-F | H | H | $CH_3$ | O | O | $s$-$C_4H_9$ |
| Cl | H | 6-F | H | H | $C_2H_5$ | O | O | $s$-$C_4H_9$ |
| Cl | H | 6-F | H | H | $i$-$C_3H_7$ | O | O | $s$-$C_4H_9$ |
| Cl | H | 6-F | H | H | $t$-$C_4H_9$ | O | O | $s$-$C_4H_9$ |
| Cl | H | 6-F | H | $CH_3$ | $CH_3$ | O | O | $s$-$C_4H_9$ |
| Cl | H | 6-Cl | $CH_3$ | H | H | O | O | $s$-$C_4H_9$ |
| Cl | H | 6-Cl | H | $CH_3$ | H | O | O | $s$-$C_4H_9$ |
| Cl | H | 6-Cl | H | H | $CH_3$ | O | O | $s$-$C_4H_9$ |
| Cl | H | 6-Cl | H | H | $C_2H_5$ | O | O | $s$-$C_4H_9$ |
| Cl | H | 6-Cl | H | H | $i$-$C_3H_7$ | O | O | $s$-$C_4H_9$ |
| Cl | H | 6-Cl | H | H | $t$-$C_4H_9$ | O | O | $s$-$C_4H_9$ |
| Cl | H | 6-Cl | H | $CH_3$ | $CH_3$ | O | O | $s$-$C_4H_9$ |
| $CH_3$ | $CH_3$ | H | $CH_3$ | H | H | O | O | $s$-$C_4H_9$ |
| $CH_3$ | $CH_3$ | H | H | $CH_3$ | H | O | O | $s$-$C_4H_9$ |
| $CH_3$ | $CH_3$ | H | H | H | $CH_3$ | O | O | $s$-$C_4H_9$ |
| $CH_3$ | $CH_3$ | H | H | H | $C_2H_5$ | O | O | $s$-$C_4H_9$ |
| $CH_3$ | $CH_3$ | H | H | H | $i$-$C_3H_7$ | O | O | $s$-$C_4H_9$ |
| $CH_3$ | $CH_3$ | H | H | H | $t$-$C_4H_9$ | O | O | $s$-$C_4H_9$ |
| $CH_3$ | $CH_3$ | H | H | $CH_3$ | $CH_3$ | O | O | $s$-$C_4H_9$ |
| $CH_3$ | $CH_3$ | 6-$CH_3$ | H | $CH_3$ | H | O | O | $s$-$C_4H_9$ |
| $CH_3$ | $CH_3$ | 6-$CH_3$ | $CH_3$ | H | H | O | O | $s$-$C_4H_9$ |
| $CH_3$ | $CH_3$ | 6-$CH_3$ | H | H | $CH_3$ | O | O | $s$-$C_4H_9$ |
| $CH_3$ | $CH_3$ | 6-$CH_3$ | H | H | $C_2H_5$ | O | O | $s$-$C_4H_9$ |
| $CH_3$ | $CH_3$ | 6-$CH_3$ | H | H | $i$-$C_3H_7$ | O | O | $s$-$C_4H_9$ |
| $CH_3$ | $CH_3$ | 6-$CH_3$ | H | H | $t$-$C_4H_9$ | O | O | $s$-$C_4H_9$ |
| $CH_3$ | $CH_3$ | 6-$CH_3$ | H | H | $CH_3$ | O | O | $s$-$C_4H_9$ |
| Cl | Cl | H | $CH_3$ | H | H | O | O | 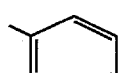 |
| Cl | Cl | H | H | $CH_3$ | H | O | O | 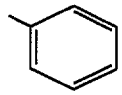 |

TABLE 3-continued
| X | Y | $Z_n$ | $R_a$ | $R_b$ | $R_c$ | L | M | $R^2$ |
|---|---|---|---|---|---|---|---|---|
| Cl | Cl | H | H | H | $CH_3$ | O | O |  |
| Cl | Cl | H | H | H | $C_2H_5$ | O | O |  |
| Cl | Cl | H | H | H | i-$C_3H_7$ | O | O |  |
| Cl | Cl | H | H | H | t-$C_4H_9$ | O | O |  |
| Cl | Cl | H | H | $CH_3$ | $CH_3$ | O | O |  |
| Cl | H | 6-F | $CH_3$ | H | H | O | O |  |
| Cl | H | 6-F | H | $CH_3$ | H | O | O |  |
| Cl | H | 6-F | H | H | $CH_3$ | O | O |  |
| Cl | H | 6-F | H | H | $C_2H_5$ | O | O |  |
| Cl | H | 6-F | H | H | i-$C_3H_7$ | O | O |  |
| Cl | H | 6-F | H | H | t-$C_4H_9$ | O | O |  |
| Cl | H | 6-F | H | $CH_3$ | $CH_3$ | O | O |  |
| Cl | H | 6-Cl | $CH_3$ | H | H | O | O |  |
| Cl | H | 6-Cl | H | $CH_3$ | H | O | O |  |

TABLE 3-continued
| X | Y | Z_n | R_a | R_b | R_c | L | M | R² |
|---|---|---|---|---|---|---|---|---|
| Cl | H | 6-Cl | H | H | CH$_3$ | O | O |  |
| Cl | H | 6-Cl | H | H | C$_2$H$_5$ | O | O |  |
| Cl | H | 6-Cl | H | H | i-C$_3$H$_7$ | O | O |  |
| Cl | H | 6-Cl | H | H | t-C$_4$H$_9$ | O | O |  |
| Cl | H | 6-Cl | H | CH$_3$ | CH$_3$ | O | O |  |
| CH$_3$ | CH$_3$ | H | CH$_3$ | H | H | O | O |  |
| CH$_3$ | CH$_3$ | H | H | CH$_3$ | H | O | O |  |
| CH$_3$ | CH$_3$ | H | H | H | CH$_3$ | O | O |  |
| CH$_3$ | CH$_3$ | H | H | H | C$_2$H$_5$ | O | O |  |
| CH$_3$ | CH$_3$ | H | H | H | i-C$_3$H$_7$ | O | O |  |
| CH$_3$ | CH$_3$ | H | H | H | t-C$_4$H$_9$ | O | O |  |
| CH$_3$ | CH$_3$ | H | H | CH$_3$ | CH$_3$ | O | O |  |
| CH$_3$ | CH$_3$ | 6-CH$_3$ | CH$_3$ | H | H | O | O |  |
| CH$_3$ | CH$_3$ | 6-CH$_3$ | H | CH$_3$ | H | O | O |  |

TABLE 3-continued
| X | Y | $Z_n$ | $R_a$ | $R_b$ | $R_c$ | L | M | $R^2$ |
|---|---|---|---|---|---|---|---|---|
| $CH_3$ | $CH_3$ | 6-$CH_3$ | H | H | $CH_3$ | O | O |  |
| $CH_3$ | $CH_3$ | 6-$CH_3$ | H | H | $C_2H_5$ | O | O |  |
| $CH_3$ | $CH_3$ | 6-$CH_3$ | H | H | i-$C_3H_7$ | O | O |  |
| $CH_3$ | $CH_3$ | 6-$CH_3$ | H | H | t-$C_4H_9$ | O | O |  |
| $CH_3$ | $CH_3$ | 6-$CH_3$ | H | H | $CH_3$ | O | O |  |
| Cl | Cl | H | $CH_3$ | H | H | O | O | 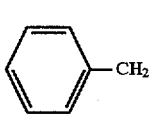 |
| Cl | Cl | H | H | $CH_3$ | H | O | O | 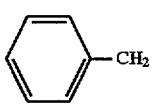 |
| Cl | Cl | H | H | H | $CH_3$ | O | O | 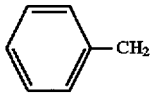 |
| Cl | Cl | H | H | H | $C_2H_5$ | O | O | 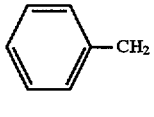 |
| Cl | Cl | H | H | H | i-$C_3H_7$ | O | O | 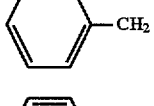 |
| Cl | Cl | H | H | H | t-$C_4H_9$ | O | O | 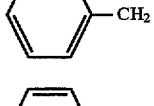 |
| Cl | Cl | H | H | $CH_3$ | $CH_3$ | O | O | 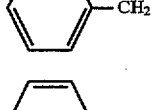 |
| Cl | H | 6-F | $CH_3$ | H | H | O | O | 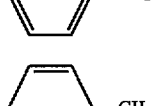 |
| Cl | H | 6-F | H | $CH_3$ | H | O | O | 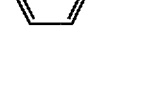 |

TABLE 3-continued
| X | Y | $Z_n$ | $R_a$ | $R_b$ | $R_c$ | L | M | $R^2$ |
|---|---|---|---|---|---|---|---|---|
| Cl | H | 6-F | H | H | $CH_3$ | O | O | 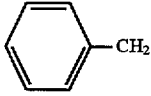 |
| Cl | H | 6-F | H | H | $C_2H_5$ | O | O | 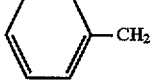 |
| Cl | H | 6-F | H | H | $i$-$C_3H_7$ | O | O | 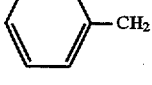 |
| Cl | H | 6-F | H | H | $t$-$C_4H_9$ | O | O | 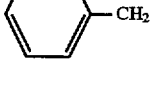 |
| Cl | H | 6-F | H | $CH_3$ | $CH_3$ | O | O | 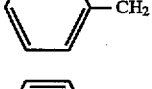 |
| Cl | H | 6-Cl | $CH_3$ | H | H | O | O | 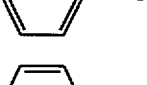 |
| Cl | H | 6-Cl | H | $CH_3$ | H | O | O | 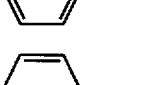 |
| Cl | H | 6-Cl | H | H | $CH_3$ | O | O | 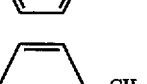 |
| Cl | H | 6-Cl | H | H | $C_2H_5$ | O | O | 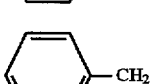 |
| Cl | H | 6-Cl | H | H | $i$-$C_3H_7$ | O | O | 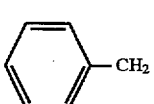 |
| Cl | H | 6-Cl | H | H | $t$-$C_4H_9$ | O | O | 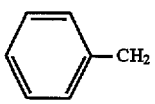 |
| Cl | H | 6-Cl | H | $CH_3$ | $CH_3$ | O | O | 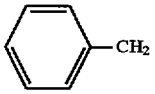 |
| $CH_3$ | $CH_3$ | H | $CH_3$ | H | H | O | O | 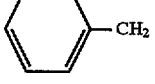 |
| $CH_3$ | $CH_3$ | H | H | $CH_3$ | H | O | O |  |

TABLE 3-continued

| X | Y | $Z_n$ | $R_a$ | $R_b$ | $R_c$ | L | M | $R^2$ |
|---|---|---|---|---|---|---|---|---|
| CH$_3$ | CH$_3$ | H | H | H | CH$_3$ | O | O | PhCH$_2$ |
| CH$_3$ | CH$_3$ | H | H | H | C$_2$H$_5$ | O | O | PhCH$_2$ |
| CH$_3$ | CH$_3$ | H | H | H | i-C$_3$H$_7$ | O | O | PhCH$_2$ |
| CH$_3$ | CH$_3$ | H | H | H | t-C$_4$H$_9$ | O | O | PhCH$_2$ |
| CH$_3$ | CH$_3$ | H | H | CH$_3$ | CH$_3$ | O | O | PhCH$_2$ |
| CH$_3$ | CH$_3$ | 6-CH$_3$ | CH$_3$ | H | H | O | O | PhCH$_2$ |
| CH$_3$ | CH$_3$ | 6-CH$_3$ | H | CH$_3$ | H | O | O | PhCH$_2$ |
| CH$_3$ | CH$_3$ | 6-CH$_3$ | H | H | CH$_3$ | O | O | PhCH$_2$ |
| CH$_3$ | CH$_3$ | 6-CH$_3$ | H | H | C$_2$H$_5$ | O | O | PhCH$_2$ |
| CH$_3$ | CH$_3$ | 6-CH$_3$ | H | H | i-C$_3$H$_7$ | O | O | PhCH$_2$ |
| CH$_3$ | CH$_3$ | 6-CH$_3$ | H | H | t-C$_4$H$_9$ | O | O | PhCH$_2$ |
| CH$_3$ | CH$_3$ | 6-CH$_3$ | H | H | CH$_3$ | O | O | PhCH$_2$ |

If, according to process (A), ethyl N-2,4-dichlorophenyl-acetyl-1-amino-4-ethylcyclohexane-carboxylate is used, the course of the process according to the invention can be represented by the following equation:

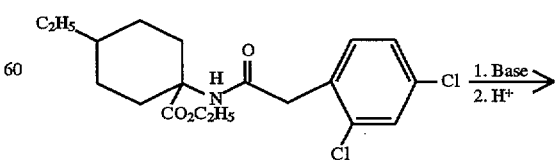

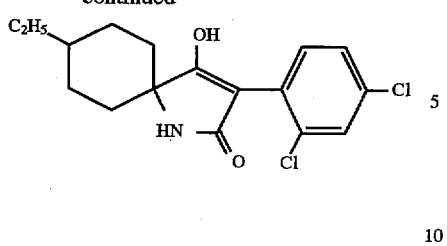

If, according to process (B) variant α), 3-(2,4,6-trimethylphenyl)-5,5-(3-methyl)-pentamethylene-pyrrolidine-2,4-dione and pivaloyl chloride are used as starting substances, the course of the process according to the invention can be represented by the following equation:

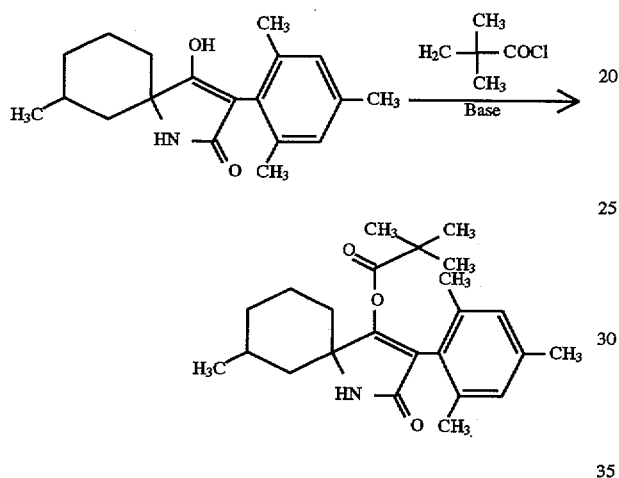

If, according to process B (variant β), 3-(2,4,6-trimethylphenyl)-5,5-(tetramethyl)-dimethylene-pyrrolidine-2,4-dione and acetic anhydride are used as starting compounds, the course of the process according to the invention can be represented by the following equation:

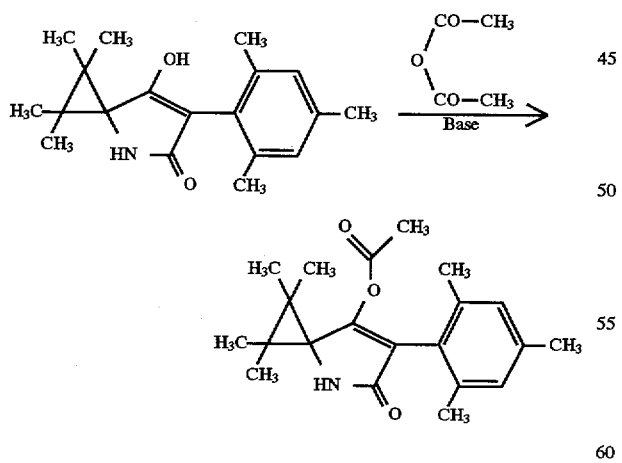

If, according to process (C), 3-(2,4,6-trimethylphenyl)-5,5-(3-methyl)-tetramethylene-pyrrolidine-2,4-dione and ethoxyethyl chloroformate are used as starting compounds, the course of the process according to the invention can be represented by the following equation.

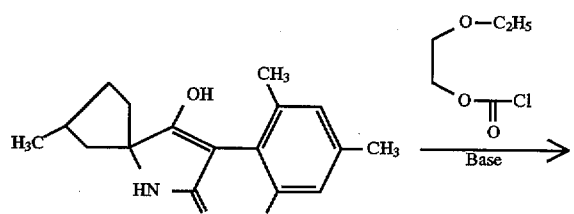

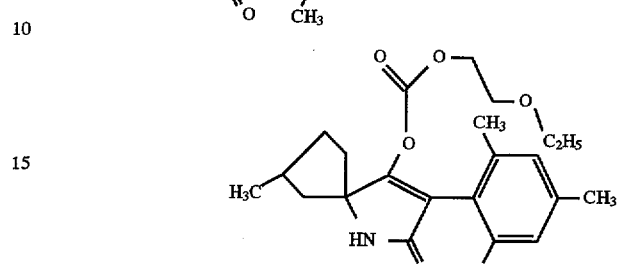

If, according to process ($D_\alpha$), 3-(2,4,6-trimethylphenyl)-5,5-(4,4-dimethyl)-pentamethylene-pyrrolidine-2,4-dione and mehyl chloromonothioformate are used as starting materials, the course of the reaction can be represented as follows:

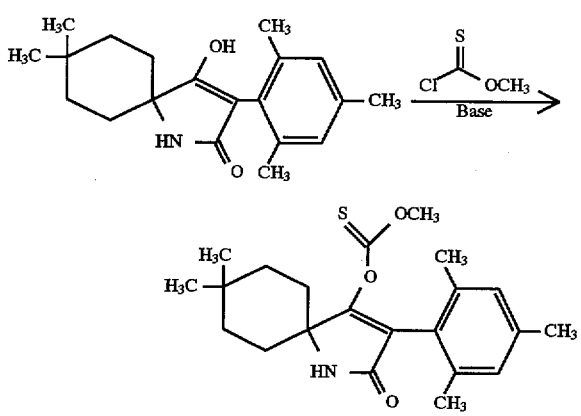

If, according to process ($D_\beta$), 3-(2,4,6-trimethylphenyl-5,5-(4-methoxy)-pentmethylene-pyrrolidne-2,4-dione, carbon disulphide and methyl iodide are used as starting components, the course of the reaction can be represented as follows:

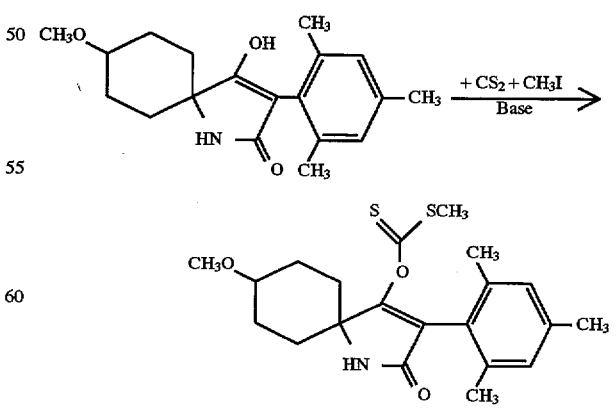

If, according to process (E), 3-(2,4,6-trimethylphenyl)-5,5-(2-methyl)-pentamethylene-pyrrolidine-2,4-dione and methanesulphonyl chloride are used as starting material, the course of the reaction can be represented by the following equation:

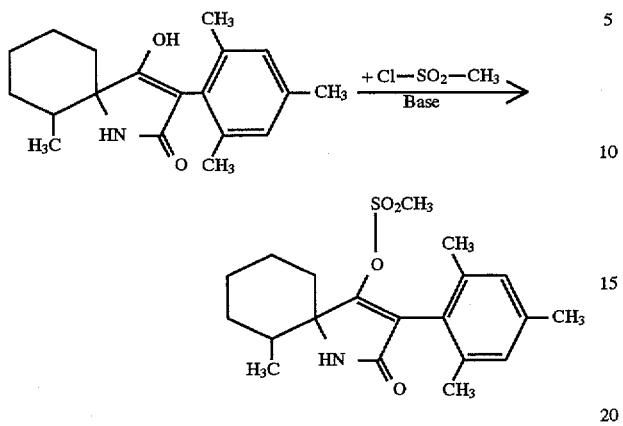

If, according to process (F), 3-(2,4-dimethylphenyl)-5,5-(3-methyl)-pentamethylene-pyrrolidine-2,4-dione and 2,2,2-trifluoroethyl methanethiochlorophosphonate are used as starting materials, the course of the reaction can be represented by the equation:

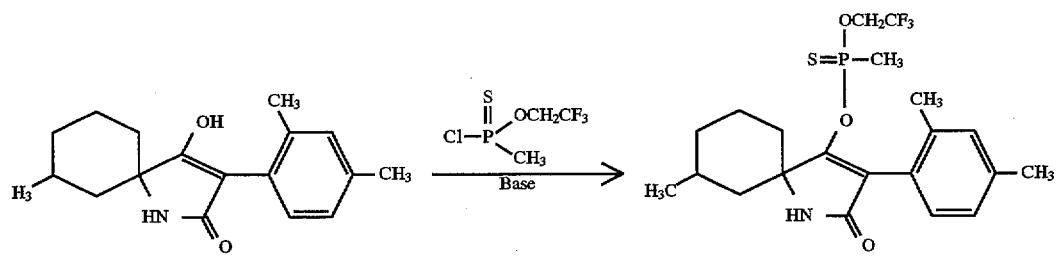

If, according to process (G), 3-(2,4,6-trimethylphenyl)-5,5-(4-tert-butyl)-pentamethylene-pyrrolidine-2,4-dione and NaOH are used as components, the course of the process according to the invention can be represented by the following equation:

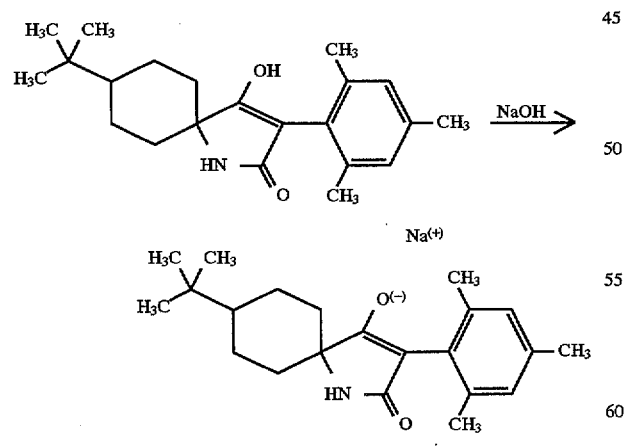

If, according to process ($H_\alpha$), 3-(2,4,6-trimethylphenyl)-5,5-(2-methyl)-pentamethylene-pyrrolidine-2,4-dione and ethyl isocyanate are used as starting materials, the course of the reaction can be represented by the following equation:

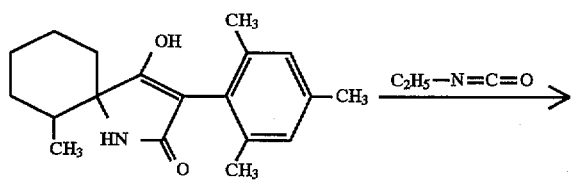

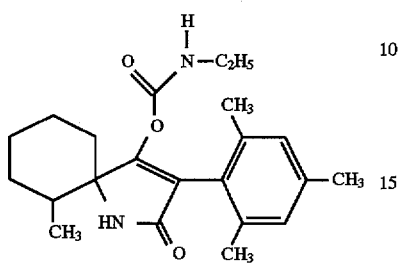

If, according to process (H_β), 3-(2,4,6-trimethylphenyl)-5,5-(3,4-dimethyl)pentamethylene-pyrrolidine-2,4-dione and dimethylcarbamoyl chloride are used as starting materials, the course of the process can be represented by the following equation:

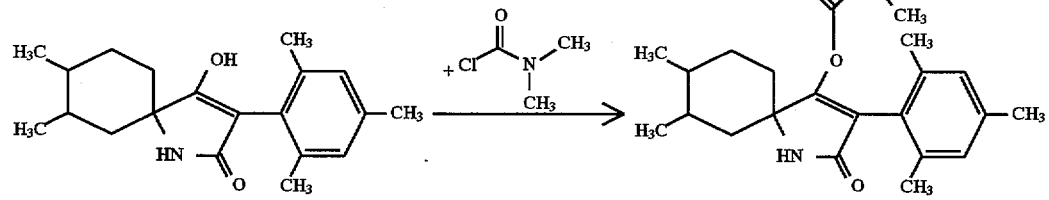

The compounds of the formula (II)

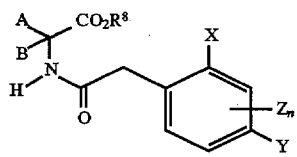 (II)

in which
A, B, X, Y, Z, n and $R^8$ have the abovementioned meaning, which are required as starting materials in processes (A) according to the invention,
are new.

Acyl-amino acid esters of the formula (II) are obtained, for example, when
amino acid derivatives of the formula (XIV)

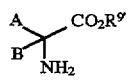 (XIV)

in which
$R^{9'}$ represents hydrogen (XIVa) and alkyl (XIVb)
and
A and B have the abovementioned meaning
are acylated (Chem. Reviews 52, 237–416 (1953); Bhattacharya, Indien J. Chem 6, 341–5, 1968)- with phenylacetyl halides of the formula (XV)

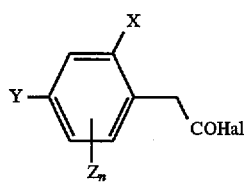 (XV)

in which
X, Y, Z and n have the abovementioned meaning and
Hal represents chlorine or bromine
or when acylamino acids of the formula (IIa)

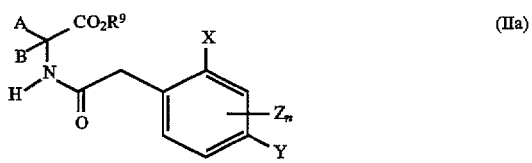 (IIa)

in which
A, B, X, Y, Z and n have the abovementioned meaning and
$R^9$ represents hydrogen
are esterified (Chem. Ind. (London) 1568 (1968)).

The substituted cyclohexylaminocarboxylic acids of the formula (XIVa) can generally be obtained in a Bucherer-Bergs reaction or by means of Strecker synthesis and they are obtained in each case in various isomeric forms. For example, the conditions of the Bucherer-Bergs reaction give mainly the isomers in which R and the carbamoyl group are positioned equatorial (hereinafter termed β for the sake of simplicity) while the conditions of Strecker synthesis give mainly the isomers in which R and the aminogroup are positioned equatorial (hereinafter termed α for the sake of simplicity).

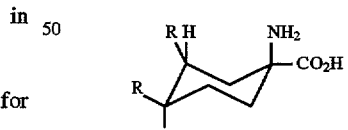

Bucher-Bergs synthesis
(β-isomer)

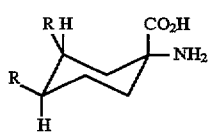

Strecker synthesis
(α-isomer)

(L. Munday, J. Chem. Soc. 4372 (1961); J. T. Eward, C. Jitrangeri, Can. J. Chem. 53, 3339 (1975).

Furthermore, the starting materials of the formula (II)

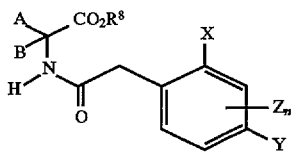

in which

A, B, X, Y, T, Z, n and R8 have the abovementioned meaning, which are used in the above processes (A), can be prepared when aminonitriles of the formula (XVI)

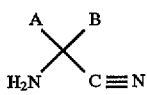

in which

A and B have the abovementioned meaning are reacted with phenylacetyl halides of the formula (XV)

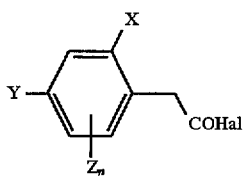

in which

X, Y, Z and n have the abovementioned meaning and Hal represents chorine or bromine,
to give compounds of the formula (XVII)

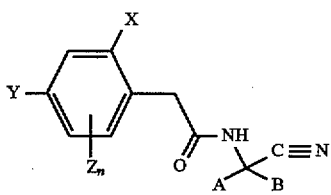

in which

A, B, X, Y, Z and n have the abovementioned meaning, and these are subsequently subjected to alcoholysis in sulphuric acid.

The compounds of the formula (XVII) are also new.

In addition to the intermediates mentioned in the preparation examples, the following compounds of the formula (II) may be mentioned by way of example but not by way of limitation:

methyl N-(2,4-dichlorphenylacetyl)-1-amino-2-methylcyclohexanecarboxylate,
methyl N-(2,4-dichlorophenylacetyl)-1-amino-3-methylcyclohexanecarboxylate,
methyl N-(2,4-dichlorophenylacetyl)-1-amino-4-methylcyclohexanecarboxylate,
methyl N-(2,4-dichlorophenylacetyl)-1-amino-3,4-dimethylcyclohexanecarboxylate,
methyl N-(2,4-dichlorophenylacetyl)-1-amino-4-ethylcyclohexanecarboxylate,
methyl N-(2,4-dichlorophenylacetyl)-1-amino-4-isopropylcyclohexanecarboxylate,
methyl N-(2,4-dichlorophenylacetyl)-1-amino-4-tert-butylcyclohexanecarboxylate,
methyl N-(2,4-dichlorophenylacetyl)-1-amino-4-phenylcyclohexanecarboxylate,
methyl N-(2,6-dichlorophenylacetyl)-1-amino-2-methylcyclohexanecarboxylate,
methyl N-(2,6-dichlorophenylacetyl)-1-amino-3-methylcyclohexanecarboxylate,
methyl N-(2,6-dichlorophenylacetyl)-1-amino-4-methylcyclohexanecarboxylate,
methyl N-(2,6-dichlorophenylacetyl)-1-amino-3,4-dimethyl-cycl2,6-dichlropheate,
methyl N-(2,6-dichlorophenylacetyl)-1-amino-4-ethylcyclohexanecarboxylate,
methyl N-(2,6-dichlorophenylacetyl)-1-amino-4-isopropylcyclohexanecarboxylate,
methyl-(2,6-dichlorophenylacetyl)-1-amino-4-tert-butylcyclohexanecarboxylate,
methyl N-(2,6-dichlorophenylacetyl)-1-amino-4-phenylcyclohexanecarboxylate,
methyl N-(2-chloro-6-fluoro-phenylacetyl)-1-amino-2-methyl-cyclohexanecarboxylate,
methyl N-(2-chloro-6-fluorophenylacetyl)-1-amino-3-methyl-cyclohexanecarboxylate,
methyl N-(2-chloro-6-fluorophenylacetyl)-1-amino-4-methyl-cyclohexanecarboxylate,
methyl N-(2-chloro-6-fluorophenylacetyl)-1-amino-3,4-dimethyl-cyclohexanecarboxylate,
methyl N-(2-chloro-6-fluorophenylacetyl)-1-amino-4-ethyl-cyclohexanecarboxylate,
methyl N-(2-chloro-6-fluorophenylacetyl)-1-amino-4-isopropyl-cyclohexanecarboxylate,
methyl N-(2-chloro-6-fluorophenylacetyl)1-amino-4-tert-butyl-cyclohexanecarboxylate,
methyl N-(2-chloro-6-fluorophenylacetyl)-1-amino-4-phenyl-cyclohexanecarboxylate,
methyl N-(2,4,6-trimethylphenylacetyl)-1-amino-2-methyl-cyclohexanecarboxylate,
methyl N-(2,4,6-trimethylphenylacetyl)-1-amino-3-methyl-cyclohexanecarboxylate,
methyl-(2,4,6-trimethylphenylacetyl)-1-amino-4-methyl-cyclohexanecarboxylate,
methyl N-(2,4,6-trimethylphenylacetyl)-1-amino-3,4-dimethyl-cyclohexanecarboxylate,
methyl N-(2,4,6-trimethylphenylacetyl)-1-amino-4-ethyl-cyclohexanecarboxylate,
methyl N-(2,4,6-trimethylphenylacetyl)-1-amino-4-isopropyl-cyclohexanecarboxylate,
methyl N-(2,4,6-trimethylphenylacetyl)-1-amino-4-tert-butyl-cyclohexanecarboxylate,
methyl N-(2,4,6-trimethylphenylacetyl)-1-amino-4-phenyl-cylcohexanecarboxylate,
methyl N-(2,4-dimethylphenylacetyl)-1-amino-2-methyl-cyclohexanecarboxylate,
methyl N-(2,4-dimethylphenylacetyl)-1-amino-3-methyl-cyclohexanecarboxylate,
methyl N-(2,4-dimethylphenylacetyl)-1-amino-4-methyl-cyclohexanecarboxylate,
methyl N-(2,4-dimethylphenylacetyl)-1-amino-3,4-dimethyl-cyclohexanecarboxylate,
methyl N-(2,4-dimethylphenylacetyl)-1-amino-4-isopropyl-cyclohexanecarboxylate;
methyl N-(2,4-dimethylphenylacetyl)-1-amino-4-tert-butyl-cyclohexanecarboxylate,
methyl N-(2,4-dimethylphenylacetyl)-1-amino-4-phenyl-cyclohexanecarboxylate, In addition to the intermediates mentioned in the preparation examples, the following compounds of the formula (IIa) may be mentioned by way of example but not by way of limitation:

N-(2,4-dichlorophenylacetyl)-1-amino-2-methyl-cyclohexanecarboxylic acid,
N-(2,4-dichlorophenylacetyl)-1-amino-3-methyl-cyclohexanecarboxylic acid, N-(2,4-dichlorophenylacetyl)-1-amino-4-methyl-cyclohexanecarboxylic acid,
N-(2,4-dichlorophenylacetyl)-1-amino-3,4-dimethyl-cyclohexanecarboxylic acid,
N-(2,4-dichlorophenylacetyl)-1-amino-4-ethyl-cyclohexanecarboxylic acid,
N-(2,4-dichlorophenylacetyl)-1-amino-4-isopropyl-cyclohexanecarboxylic acid,
N-(2,4-dichlorophenylacetyl)-1-amino-4-tert-butyl-cyclohexanecarboxylic acid,
N-(2,4-dichlorophenylacetyl)-1-amino-4-phenyl-cyclohexanecarboxylic acid,
N-(2,6-dichlorophenylacetyl)-1-amino-2-methyl-cyclohexanecarboxylic acid,
N-(2,6-dichlorophenylacetyl)-1-amino-3-methyl-cyclohexanecarboxylic acid,
N-(2,6-dichlorophenylacetyl)-1-amino-4-methyl-cyclohexanecarboxylic acid,
N-(2,6-dichlorophenylacetyl)-1-amino-3,4-dimethyl-cyclohexanecarboxylic acid,
N-(2,6-dichlorophenylacetyl)-1-amino-4-ethyl-cyclohexanecarboxylic acid,
N-(2,6-diclorophenylacetyl)-1-amino-4-isopropyl-cyclohexanecarboxylic acid,
N-(2,6-dichlorophenylacetyl)-1-amino-4-tert-butyl-cyclohexanecarboxylic acid,
N-(2,6-dichlorophenylacetyl)-1-amino-4-phenyl-cyclohexanecarboxylic acid,
N-(2-chloro-6-fluorophenylacetyl)-1-amino-2-methylcyclohexanecarboxylic acid,
N-(2-chloro-6-fluorophenylacetyl)-1-amino-3-methylcyclohexanecarboxylic acid,
N-(2-chloro-6-fluorophenylacetyl)-1-amino-4-methylcyclohexanecarboxylic acid,
N-(2-chloro-6-fluorophenylacetyl)-1-amino-3,4-dimethylcyclohexanecarboxylic acid,
N-(2-chloro-6-fluorophenylacetyl)-1-amino-4-ethyl-cyclohexanecarboxylic acid,
N-(2-chloro-6-fluorophenylacetyl)-1-amino-4-isopropyl-cyclohexanecarboxylic acid,
N-(2-chloro-6-fluorophenylacetyl)-1-amino-4-tert-butyl-cyclohexanecarboxylic acid,
N-(2-chloro-6-fluorophenylacetyl)-1-amino-4-phenyl-cyclohexanecarboxylic acid,
N-(2,4,6-trimethylphenylacetyl)-1-amino-2-methyl-cyclohexanecarboxylic acid,
N-(2,4,6-trimethylphenylacetyl)-1-amino-3-methyl-cyclohexanecarboxylic acid,
N-(2,4,6-trimethylphenylacetyl)-1-amino-4-methyl-cyclohexanecarboxylic acid,
N-(2,4,6-trimethylphenylacetyl)-1-amino-3,4-dimethylcyclohexanecarboxylic acid,
N-(2,4,6-trimethylphenylacetyl)-1-amino-4-ethyl-cyclohexanecarboxylic acid,
N-(2,4,6-trimethylphenylacetyl)-1-amino-4-isopropyl-cyclohexanecarboxylic acid,
N-(2,4,6-trimethylphenylacetyl)-1-amino-4-tert-butylcyclohexanecarboxylic acid,
N-(2,4,6-trimethylphenylacetyl)-1-amino-4-phenyl-cyclohexanecarboxylic acid,
N-(2,4-dimethylphenylacetyl)-1-amino-2-methyl-cyclohexanecarboxylic acid,
N-(2,4-dimethylphenylacetyl)-1-amino-3-methyl-cyclohexanecarboxylic acid,
N-(2,4-dimethylphenylacetyl)-1-amino-4-methyl-cyclohexanecarboxylic acid,
N-(2,4-dimethylphenylacetyl)-1-amino-3,4-dimethyl-cyclohexanecarboxylic acid,
N-(2,4-dimethylphenylacetyl)-1-amino-4-ethyl-cyclohexanecarboxylic acid,
N-(2,4-dimethylphenylacetyl)-1-amino-4-isopropyl-cyclohexanecarboxylic acid,
N-(2,4-dimethylphenylacetyl)-1-amino-4-tert-butyl-cyclohexanecarboxylic acid,
N-(2,4-dimethylphenylacetyl)-1-amino-4-phenyl-cyclohexanecarboxylic acid, Compounds of the formula (IIa) can be obtained, for example, from the phenylacetyl halides of the formula (XV) and amino acids of the formula (XIVa) by the method of Schotten-Baumann (Organikum [Laboratory Practical in Organic Chemistry], 9th Edition, 446 (1970) VEB Deutscher Verlag der Wissenschaften, Berlin).

The acid halides of the formula (III), carboxylic anhydrides of the formula (IV), chloroformic esters or chloroformic thioesters of the formula (V), chloromonothioformic esters or chlorodithioformic esters of the formula (VI), alkyl halides of the formula (VII), sulphonyl chlorides of the formula (VIII), phosphorus compounds of the formula (IX) and metal hydroxides or amines of the formula (X) and (XI) and isocyanates or carbomoyl chloride of the formula (XIII), all of which are furthermore required as starting materials for carrying out processes (B), (C), (D), (E), (F), (G) and H according to the invention, are generally compounds of organic, or inorganic, chemistry.

Process (A) is characterised in that compounds of the formula (II) in which A, B, X, Y, Z, n and $R^8$ have the abovementioned meaning are subjected to an intramolecular condensation reaction in the presence of bases.

Diluents which can be employed in process (A) according to the invention are all inert organic solvents. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide and N-methylpyrrolidone, and also alcohols such as methanol, ethanol, propanol, isopropanol, butanol, iso-butanol and tert.-butanol.

Bases (deprotonating agents) which can be employed for carrying out process (A) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates such as sodium hydroxide, potassium hydroxide, magnesium oxide, calcium oxide, sodium carbonate, potassium carbonate and calcium carbonate, sodium carbonate, potassium carbonate and calcium carbonate, all of which can also be employed in the presence of phase transfer catalysts such as, for example, triethylbenzylammonium chloride, tetrabutylammonium bromide, Adogen 464 or TDA 1*). Alkali metals such as sodium or potassium can also be used. Furthermore, alkali metal amides, alkali metal hydrides, alkaline earth metal amides and alkaline earth metal hydrides such as sodium amide, sodium hydride and calcium hydride, and moreover also alkali metal alcoholates such as sodium methylate, sodium ethylate and potassium tert.-butylate, can also be employed.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formula (II) and the deprotonating bases are generally employed in approximately twice the equimolar amounts. However, it is possible to use one or the other component in a larger excess (up to 3 mol).

Process (Bα) is characterised in that compounds of the formula (Ia) are reacted with carboxylic halides of the \* Adogen 464=methyltrialkyl ($C_8$–$C_{10}$) ammonium chloride. TDA 1=tris-(methoxyethoxyethyl)-amine formula (III).

When the acid halides are used, then diluents which can be employed in process (Bα) according to the invention are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylates such as ethyl acetate, and also strongly polar solvents such as dimethyl sulphoxide and sulpholane. If the acid halide is sufficiently stable to hydrolysis, the reaction can also be carried out in the presence of water.

If the corresponding carboxylic acid halides are used, then acid-binding agents which are suitable for the reaction in process (Bα) according to the invention are all customary acid acceptors. The following can preferably be used: tertiary amines such as triethylamine, pyridine, diazabiyclooctane (DABCO), diazabicycloundecene (DBU), diazabicyclonene (DBN), Hünig base and N,N-dimethyl-aniline, furthermore alkaline earth metal oxides such as magnesium oxide and calcium oxide, moreover alkali metal carbonate and alkaline earth metal carbonates such as sodium carbonate, potassium carbonate and calcium carbonate, and also alkali metal hydroxides such as sodium hydroxide and potassium hydroxide.

In process (Bα) according to the invention, too, the reaction temperatures can also be varied within a substantial range when carboxylic acid halides are used. In general, the process is carried out at temperatures between −20° C. and +150° C., preferably between 0° C. and 100° C.

When carrying out the process (Bα) according to the invention, the starting materials of the formula (Ia) and the carboxylic acid halide of the formula (III) are generally used in approximately equivalent amounts. However, it is also possible to employ the carboxylic anhydride in a larger excess (up to 5 mol). Working-up is carried out by customary methods.

Process (Bβ) is characterised in that compounds of the formula (Ia) are reacted with carboxylic acid hydrides of the formula (IV).

If, in process (Bβ), according to the invention, carboxylic anhydrides are used as reactant of the formula (IV), then diluents which can preferably be used are those which are also preferably suitable when acid halides are used. Apart from this, a carboxylic acid hydride employed in excess can also simultaneously act as a diluent.

When carrying out the process (Bβ) according to the invention, the reaction temperatures can also be varied within a substantial range when carboxylic anhydrides are used. In general, the process is carried out at temperatures between −20° C. and +150° C., preferably between 0° C. and 100° C.

When carrying out the process according to the invention, the starting materials of the formula (Ia) and the carboxylic anhydride of the formula (IV) are generally employed in approximately equivalent amounts. However, it is also possible to employ the carboxylic anhydride in a larger excess (up to 5 mol). Working-up is carried out by customary methods.

In general, a procedure is followed in which diluent and an excess of carboxylic anhydride as well as the carboxylic acid which forms are removed by distillation or by washing with an organic solvent or with water.

Process (C) is characterised in that compounds of the formula (Ia) are reacted with chloroformic esters or chloroformic thioesters of the formula (V).

If the corresponding chloroformic esters, or chloroformic thioesters, are used, then acid-binding agents which are suitable for the reaction in process (C) according to the invention are all customary acid acceptors. The following can preferably be used: tertiary amines such as triethylamine, pyridine, DABCO, DBU, DBA, Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, as well as alkali metal hydroxides such as sodium hydroxide and potassium hydroxide.

If the chloroformic esters, or chloroformic thioesters, are used, then diluents which can be employed in process (C) according to the invention are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylates such as ethyl acetate, and also strongly polar solvents such as dimethyl sulphoxide and sulpholane.

If the chloroformic esters, or chloroformic thioesters, are used as carboxylic acid derivatives of the formula (V), then the reaction temperatures for carrying out process (C) according to the invention can be varied within a substantial range. If the process is carried out in the presence of a diluent and of an acid-binding agent, the reaction temperatures are generally between −20° C. and +100° C. preferably between 0° C. and 50° C.

Process (C) according to the invention is generally carried out under atmospheric pressure.

When carrying out process (C) according to the invention, the starting materials of the formula (Ia) and the corresponding chloroformic ester, or chloroformic thioester, of the formula (V) are generally used in approximately equivalent amounts. However, it is also possible to employ one or the other component in a larger excess (up to 2 mol). Working-up is carried out by customary methods. In general, a procedure is followed in which the salts which have precipitated are removed and the reaction mixture which remains is concentrated by stripping off the diluent.

In preparation process (D), approximately one mol of chloromonothioformic ester, or chlorodithioformic ester, of the formula (VI) is reacted per mole of starting compound of the formula (Ia) at 0° to 120° C., preferably at 20° to 60° C.

Suitable diluents which are optionally added are all inert polar organic solvents such as ethers, amides, sulphones and sulphoxides.

Dimethyl sulphoxide, tetrahydrofuran, dimethylformamide and dimethyl sulphide are preferably employed.

If, in a preferred embodiment, the enolate salt of the compound Ia is prepared by an addition of strong deprotonating agents such as, for example, sodium hydride or potassium tertiary butylate, a further addition of acid-binding agents can be dispensed with.

If acid-binding agents are employed, then suitable substances are customary inorganic or organic bases, sodium hydroxide, sodium carbonate, potassium carbonate, pyridine and triethylamine being mentioned by way of example.

The reaction can be carried out under atmospheric pressure or increased pressure, it is preferably carried out under atmospheric pressure. Working-up is carried out by customary methods.

In preparation process ($D_\beta$), an aquimolar amount, or an excess, of carbon disulphide is added per mole of starting compound of the formula (Ia). This process is preferably carried out at temperatures from 0° to 50° C. and, in particular, at 20° to 30° C.

It is frequently expedient to first prepare the corresponding salt from the compound of the formula (Ia) by adding a deprotonating agent (such as, for example, potassium tertiary butylate or sodium hydride). The compound (Ia) is reacted with carbon disulphide until the formation of the intermediate is complete, for example after stirring at room temperature for several hours.

The product is further reacted with the alkyl halide of the formula (VII) at preferably 0° to 70° C. in particular at 20° to 50° C. At least an aquimolar amount of alkyl halide is employed in this process.

The process is carried out at atmospheric pressure or under increased pressure, preferably under atmospheric pressure.

Again, working-up is carried out by customary methods.

In preparation process (E), approximately one mol of sulphonyl chloride (VIII) is reacted per mole of starting compound of the formula (Ia) at −20° to 150° C., preferably at 11° to 70° C.

Suitable diluents which are optionally added are all inert polar organic solvents such as ethers, amides, nitriles, sulphones, sulphoxides or halogenated hydrocarbons such as methylene chloride.

Dimethyl sulphoxide, tetrahydrofuran, dimethylformamide, dimethyl sulphide and methyloene chloride are preferably employed.

If, in a preferred embodiment, the enolate salt of the compound Ia is prepared by adding strong deprotonating agents (such as, for example, sodium hydride or potassium tertiary butylate), a further addition of acid-binding agents can be dispensed with.

If acid-binding agents are employed, then suitable substances are customary inorganic or organic bases, sodium hydroxide, sodium carbonate, potassium carbonate, pyridine and triethylamine being mentioned by way of example.

The reaction can be carried out under atmospheric pressure or under increased pressure, it is preferably carried out under atmospheric pressure. Working-up is carried out by customary methods.

To obtain compounds of the structure (Ie) in preparation process (F), 1 to 2, preferably 1 to 1.3 mol of the phosphorus compound of the formula (IX) are reacted per mole of the compound (Ia) at temperatures between −40° C. and 150° C., preferably between −10° and 110° C.

Suitable diluents which are optionally added are all inert polar organic solvents such as ethers, amides, nitriles, alcohols, sulphides, sulphones, sulphoxides and the like.

Acetonitrile, dimethyl sulphoxide, tetrahydrofuran, dimethylformamide and methylene chloride are preferably employed.

Suitable acid-binding agents which are optionally added are customary inorganic or organic bases such as hydroxides or carbonates. Examples which may be mentioned are sodium hydroxide, sodium carbonate, potassium carbonate, pyridine and triethylamine.

The reaction can be carried out under atmospheric pressure or under increased pressure, it is preferably carried out under atmospheric pressure. Working-up is carried out by customary methods of organic chemistry. The end products obtained are preferably purified by crystallisation, chromatographic purification or so-called "incipient distillation", i.e. removal of the volatile components in vacuo.

Process (G) is characterised in that compounds of the formula (Ia) are reacted with metal hydroxides (X) or amines (XI).

Diluents which can be employed in the process according to the invention are, preferably, ethers such as tetrahydrofuran, dioxane, diethyl ether, or else alcohols such as methanol, ethanol, isopropanol, but also water. Process (G) according to the invention is generally carried out under atmospheric pressure. The reaction temperatures are generally between −20° C. and 100° C., preferably between 0° C. and 50° C.

In preparation process ($H_\alpha$), approximately 1 mol of isocyanate of the formula (XII) is reacted-per mole of starting compound of the formula (Ia) at 0° to 100° C., preferably at 20° to 50° C.

Suitable diluents which are optionally added are all inert organic solvents such as ethers, amides, nitriles, sulphones or sulphoxides.

If appropriate, catalysts can be added to accelerate the reaction. Catalysts which can be employed very advantageously are organotin compounds such as, for example, dibutyltin dilaurate. The process is preferably carried out under atmospheric pressure.

In preparation process ($H_\beta$), approximately 1 mol of carbamoyl chloride of the formula (XIII) is reacted per mole of starting compound of the formula (Ia) at 0° to 150° C., preferably at 20° to 70° C.

Suitable diluents which are optionally added, are all inert polar organic solvents such as ethers, amides, sulphones or sulphoxides.

Dimethyl sulphoxide, tetrahydrofuran, dimethylformamide or methylene chloride are preferably employed.

If, in a preferred embodiment, the enolate salt of the compound (Ia) is prepared by adding strong deprotonating agents (such as, for example, sodium hydride or potassium tertiary butylate), a further addition of acid-binding agents can be dispensed with.

If acid-binding agents are employed, then suitable substances are customary inorganic or organic bases, sodium hydroxide, sodium carbonate, potassium carbonate, triethylamine or pyridine being mentioned by way of example.

The reaction can be carried out under atmospheric pressure or under increased pressure, it is preferably carried out under atmospheric pressure. Working-up is carried out by customary methods.

The active compounds are suitable for combating animal pests, preferably arthropods and nematodes, in particular insects and arachnids, which occur in agriculture, in forests, in the protection of stored products and of materials, and in the hygiene sector. They are active against normally sensitive and resistant species and against all or individual development stages. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutiger-*

*ella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp..*

From the order of the Anoplura, for example, *Phylloxera vastatrix, Pemphigus spp., Pediculus humanus corporis, Haematopinus spp.* and *Linognathus spp..*

From the order of the Mallophaga, for example, *Trichodectes spp.* and *Damalinea spp..*

From the order of the Thysanoptera, for example, *Hercino-thrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyaiopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. Psylla spp..*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varive stis, Atomaria spp., Oryzaephilus surinamensis, Antho nomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Cono derus spp., Melolontha melolontha, Amphimallon solsti tialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster,*
*Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp..*

From the order of the Arachnida, for example, *Scorpo maurus* and *Latrodectus mactans.*

From the order of the Acarina, for example, *Acarus siro, Argas spp., Ornithodoros spp., Dermanyssus gallinae., Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Byrobia praetiosa, Panonychus spp., Tetranychus spp..*

The active compounds according to the invention are distinguished by a higher insecticidal and acaricidal activity.

They can be used particularly successfully for combating insects which are harmful to plants such as, for example, against the larvae of the mustard beetle (*Phaedon cochleariae*) or against the larvae of the green rice cicada (*Nephotettix cincticeps*) against the caterpillars of the cabbage moth *Phutella maculipennis.*

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Stirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are highly suitable for selectively combating monocotyledon weeds in dicotyledon cultures by the pre- and post-emergence methods. They can be employed highly successfully for example in cotton or sugar beet for combating grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkyl-aryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soya beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one-2,2-dioxide (BENTAZONE); methyl5-(2,4-dichlorophenoxy)-2-nitrobenzoate (BIFENOX); 3,5-dibromo-4-hydroxy-benzonitrile (BROMOXYNIL); 2-chloro-N-[(4-methoxy-6-methyl-1,3,5-triazin-2-yl)-amino]-carbonyl-benzenesulphonamide (CHLORSULFURON); 2-[4-(2,4-dichlorophenoxy)-phenoxy]-propionic acid, its methyl ester or its ethyl ester (DICLOFOP-METHYL); 4-amino-6-t-butyl-3-ethylthio-1, 2,4-triazin-5(4H)-one (ETHIOZIN); 2-4-[(6-chloro-2-benzoxazolyl)-oxy]-phenoxy -propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidizol-2-yl]-4(5)-methylbenzoate (IMAZAMETHABENZ); 3,5-diiodo-4-hydroxybenzotrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-[[((4-methoxy-6-methyl-1,3,5-triazin-2-yl)-amino)-carbonyl]-amino]-sulphonyl -benzoic acid or its (METSULFURON); N-(1-ethylpropyl)-3,4-dimethyl-2,6-dinitroaniline (PENDIMETHALIN); 0-(6-chloro-3-phenyl-pyridazin-4-yl) S-octyl thiocarbonate (PYRIDATE); 4-ethylamino-2-t-butylamino-6-methylthio-s-triazine (TERBUTRYN); 3-[[[[(4-methoxy-6-methyl-1,3,5-triazin-2-yl)-amino]-carbonyl]-amino]-sulphonyl]-thiophene-2-carboxylic acid (THIAMETURON); are also possible. Surprisingly, some mixtures also show a synergistic action.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example (Ia-1)

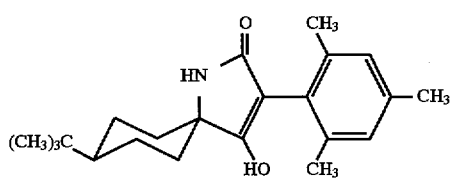

4.14 g (0.138 mol) of sodium hydride are suspended in 70 ml of absolute toluene and the mixture is refluxed. 25.6 g (0.069 mol) of methyl N-(2,4,6-trimethylphenylacetyl)-1-amino-4-t.-butyl-cyclohexanecarboxylate in 140 ml of absolute toluene are added dropwise and the mixture is subsequently refluxed until the reaction has ended (checked by thin-layer chromatography). After the mixture has cooled to room temperature, ethanol is added dropwise, with ice-cooling, until no more hydrogen evolves. The solvent is then evaporated, the residue is taken up in ethanol, and the mixture is stirred into approx. 10% strength hydrochloric acid at 0°–20° C. The solid which has precipitated is filtered off with suction and dried.

After recrystallisation from chloroform/hexane, 14.90 g (63% of theory) of 3(2,4.,6-trimethylphenyl)-5,5-(4-t-butyl)-pentamethylene-pyrrolidine-2,4-dione of melting point m.p.: >220° C. are obtained (β-isomer).

Example (Ia-2)

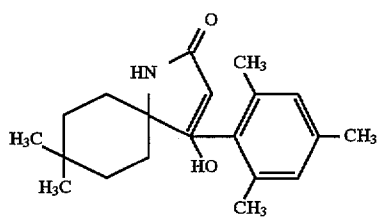

37.2 g (0.331 mol) of potassium tert.-butylate are heated at reflux temperature in 100 ml of absolute tetrahydrofuran. 52 g (0.151 mol) of methyl N-(2,4,6-trimethylphenylacetyl)-1-amino-4,4-dimethyl-cyclohexanecarboxylate in 510 ml of absolute toluene are added dropwise, and the mixture is refluxed for 90 minutes. When the reaction has ended, the batch is brought to room temperature, and 500 ml of water are added. The aqueous phase is separated off, and the toluene phase is extracted using 220 ml of water. The combined aqueous phases are washed with toluene and subsequently treated with 50 ml of concentrated hydrochloric acid at room temperature. The solid which has precipitated is filtered with suction, washed and dried. To purify the crude product further, it is suspended in 300 ml of methyl tert.-butyl ether and subjected to filtration suction. 44.9 g (95% of theory) of 3-(2,4,6-trimethylphenyl)-5,5-(4,4-dimethyl)-pentamethylene-pyrrolidine-2,4-dione of melting point m.p.:>220° C. are obtained.

The following end products of the formula (Ia) which are listed in Table 4 are obtained analogously to Example (Ia-1) and (Ia-2) and following the general information in the description for the processes according to the invention, in the form of the α-isomer or the β-isomer:

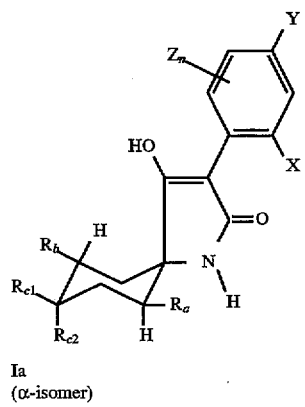

Ia (α-isomer)

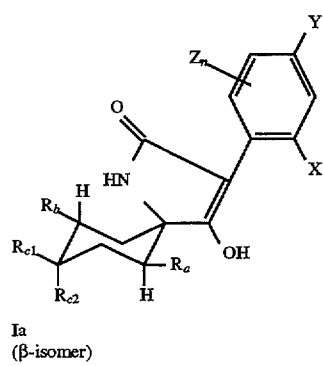

Ia (β-isomer)

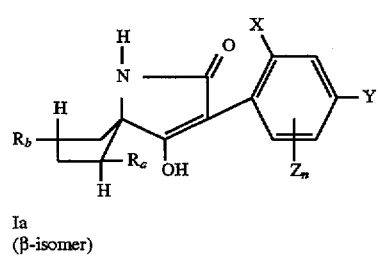

Ia (β-isomer)

TABLE 4

| Ex. No. | X | Y | $Z_n$ | $R_a$ | $R_b$ | $R_{c1}$ | $R_{c2}$ | Physical constant | Note |
|---|---|---|---|---|---|---|---|---|---|
| (Ia-3) | Cl | Cl | H | $CH_3$ | H | H | H | 146 | αa |
| (Ia-4) | $CH_3$ | $CH_3$ | 6-$CH_3$ | $CH_3$ | H | H | H | >220 | a |
| (Ia-5) | $CH_3$ | $CH_3$ | 6-$CH_3$ | H | H | $CH_3$ | H | >220 | α |
| (Ia-6) | $CH_3$ | $CH_3$ | 6-$CH_3$ | H | $CH_3$ | H | H | 217 | α |
| (Ia-7) | Cl | Cl | H | H | $CH_3$ | $CH_3$ | H | 130–140 | α |
| (Ia-8) | $CH_3$ | $CH_3$ | 6-$CH_3$ | H | $CH_3$ | $CH_3$ | H | >220 | α |
| (Ia-9) | $CH_3$ | $CH_3$ | H | H | H | $CH_3$ | H | 190–198 | α |

TABLE 4-continued

| Ex. No. | X | Y | $Z_n$ | $R_a$ | $R_b$ | $R_{c1}$ | $R_{c2}$ | Physical constant | Note |
|---|---|---|---|---|---|---|---|---|---|
| (Ia-10) | $CH_3$ | $CH_3$ | 6-$CH_3$ | H | $CH_3$ | H | H | 120 | β |
| (Ia-11) | $CH_3$ | $CH_3$ | 6-$CH_3$ | H | H | $CH_3$ | H | >220 | β |
| (Ia-12) | Cl | Cl | H | H | $CH_3$ | H | H | >220 | α |
| (Ia-13) | Cl | Cl | H | H | $CH_3$ | H | H | 207–209 | β |
| (Ia-14) | $CH_3$ | $CH_3$ | H | H | $CH_3$ | H | H | 188–499 | β |
| (Ia-15) | Cl | Cl | H | H | H | $CH_3$ | H | 205–207 | α |
| (Ia-16) | $CH_3$ | $CH_3$ | 6-$CH_3$ | H | H | $C_2H_5$ | H | 149–200 | α |
| (Ia-17) | $CH_3$ | $CH_3$ | 6-$CH_3$ | H | H | $C_2H_5$ | H | 196–202 | β |
| (Ia-18) | Cl | Cl | H | H | H | $C_2H_5$ | H | 212–213 | α |
| (Ia-19) | Cl | Cl | H | H | H | $CH_3$ | H | >220 | β |
| (Ia-20) | $CH_3$ | $CH_3$ | H | H | H | $CH_3$ | H | >220 | β |
| (Ia-21) | Cl | Cl | H | H | H | $C_2H_5$ | H | 235 | β |
| (Ia-22) | $CH_3$ | $CH_3$ | 6-$CH_3$ | —$CH_2$— | | H | H | >220 | α |
| (Ia-23) | Cl | Cl | H | —$CH_2$— | | H | H | 214–217 | α |
| (Ia-24) | $CH_3$ | $CH_3$ | 6-$CH_3$ | $CH_3$ | H | — | — | 183–185 | α |
| (Ia-25) | $CH_3$ | $CH_3$ | 6-$CH_3$ | H | $CH_3$ | — | — | >220 | α |
| (Ia-26) | $CH_3$ | $CH_3$ | 6-$CH_3$ | H | H | $C_6H_{11}$ | H | >260 | α |
| (Ia-27) | $CH_3$ | $CH_3$ | 6-$CH_3$ | H | H | $C_6H_{11}$ | H | 252–253 | β |
| (Ia-28) | $CH_3$ | $CH_3$ | 6-$CH_3$ | H | H | $C_6H_5$ | H | >230 | α |
| (Ia-29) | $CH_3$ | $CH_3$ | 6-$CH_3$ | H | H | —$(CH_2)_5$— | | >220 | — |
| (Ia-30) | $CH_3$ | $CH_3$ | 6-$CH_3$ | H | H | i-$C_3H_7$ | H | 239–240 | α |
| (Ia-31) | $CH_3$ | $CH_3$ | 6-$CH_3$ | H | H | O—$CH_3$ | H | >220 | α |
| (Ia-32) | $CH_3$ | $CH_3$ | 6-$CH_3$ | H | H | O—$CH_3$ | H | >220 | β |
| (Ia-33) | $CH_3$ | $CH_3$ | H | H | H | $C_2H_5$ | H | 186 | β |
| (Ia-34) | Cl | Cl | H | H | H | $C_3H_7$ | H | 182 | β |
| (Ia-35) | $CH_3$ | $CH_3$ | H | H | H | $C_3H_7$ | H | 197 | β |
| (Ia-36) | $CH_3$ | $CH_3$ | 6-$CH_3$ | H | H | $C_3H_7$ | H | 206 | β |
| (Ia-37) | $CH_3$ | $CH_3$ | H | H | H | i-$C_3H_7$ | H | 196–205 | β |
| (Ia-38) | $CH_3$ | $CH_3$ | 6-$CH_3$ | H | H | i-$C_3H_7$ | H | 214 | β |

Example (Ib-1)

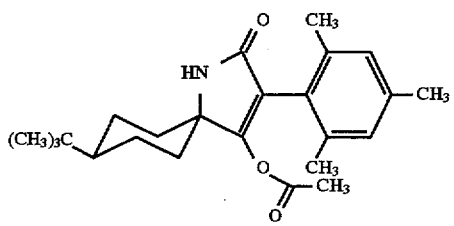

5.12 g (0.015 mol) of 3-(2,4,6-trimethylphenyl)-5,5-(4-t.-butyl)-pentamethylene-pyrrolidine-2,4-dione are dissolved in 60 ml of absolute dichloromethane, and 2.1 ml of trimethylamine are added. 1.13 ml of acetyl chloride in 5 ml of absolute dichoromethane are added at 0° to 10° C. The end of the reaction is determined by thin-layer chromatography. The mixture is washed subsequently twice with 100 ml portions of 0.5N sodium hydroxide solution, and the organic phase is dried over magnesium sulphate. The residue which is obtained after the solvent has been evaporated is recrystallised from ethyl acetate/n-hexane.

2 g(35% of theory) of 3-(2,4,6-trimethylphenyl)-5,5-(4-t.-butyl)-pentamethylene-4-acetyloxy-Δ3-pyrolin-2-one of melting point m.p.:>220° C. are obtained. (β-isomer).

Example (Ib-2)

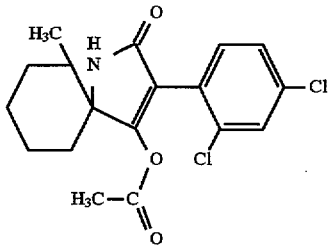

3-(2,4-dichlorphenyl)-5,5-(2-methyl)-pentamethylene-4-acetyloxy-Δ3-pyrrolin-2-one of melting point m.p.: 138° C. (isomer mixture) is obtained analogously to Example (Ib-1).

The end products of the formula (Ib) listed below in Table 5 are obtained analogously to Example (Ib-1) and (Ib-2) and following the general information in the description for the processes according to the invention in the form of the α-isomer or the β-isomer.

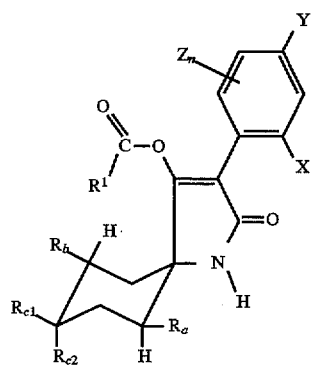

Ib
(α-isomer)

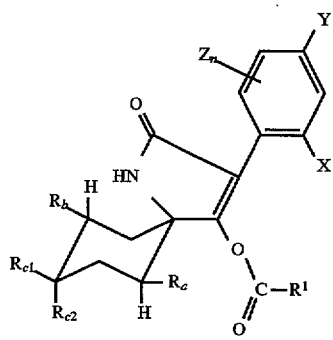

Ib
(β-isomer)

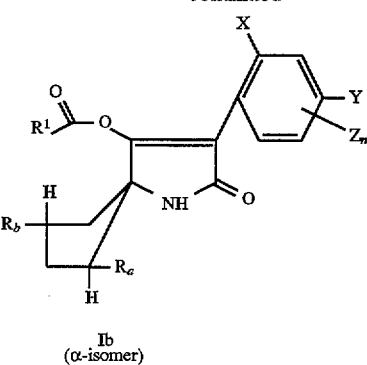

Ib
(α-isomer)

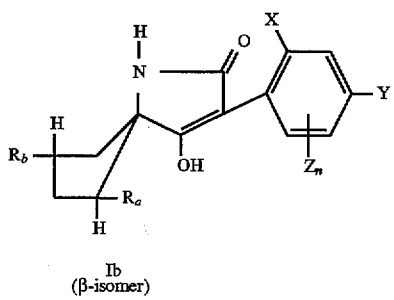

Ib
(β-isomer)

TABLE 5

| Ex. No. | X | Y | $Z_n$ | $R_a$ | $R_b$ | $R_{c1}$ | $R_{c2}$ | $R^1$ | physical const. mp.: °C. | Isomer |
|---|---|---|---|---|---|---|---|---|---|---|
| (Ib-3) | $CH_3$ | $CH_3$ | 6-$CH_3$ | $CH_3$ | H | H | H | $CH_3$ | 218 | α |
| (Ib-4) | $CH_3$ | $CH_3$ | 6-$CH_3$ | H | H | $CH_3$ | H | $CH_3$ | >220° | α |
| (Ib-5) | $CH_3$ | $CH_3$ | 6-$CH_3$ | $CH_3$ | H | H | H | t-$C_4H_9$ | 180 | α |
| (Ib-6) | $CH_3$ | $CH_3$ | 6-$CH_3$ | H | $CH_3$ | $CH_3$ | H | i-$C_3H_7$ | 215 | α |
| (Ib-7) | Cl | Cl | H | H | $CH_3$ | H | H | i-$C_3H_7$ | 146–147 | α |
| (Ib-8) | Cl | Cl | H | H | $CH_3$ | H | H | $CH_3$ | 191 | α |
| (Ib-9) | $CH_3$ | $CH_3$ | 6-$CH_3$ | H | $CH_3$ | H | H | $CH_3$ | 214 | α |
| (Ib-10) | $CH_3$ | $CH_3$ | 6-$CH_3$ | H | $CH_3$ | H | H | i-$C_3H_7$ | 221 | α |
| (Ib-11) | $CH_3$ | $CH_3$ | 6-$CH_3$ | H | $CH_3$ | H | H | $CH_3$ | 220 | β |
| (Ib-12) | $CH_3$ | $CH_3$ | 6-$CH_3$ | H | H | $CH_3$ | H | $CH_3$ | >220 | β |
| (Ib-13) | $CH_3$ | $CH_3$ | 6-$CH_3$ | H | $CH_3$ | H | H | t-$C_4H_9$ | 228 | α |
| (Ib-14) | Cl | Cl | H | H | $CH_3$ | H | H | $CH_3$ | 217–218 | β |
| (Ib-15) | Cl | Cl | H | H | $CH_3$ | H | H | i-$C_3H_7$ | 162–163 | β |
| (Ib-16) | Cl | Cl | H | H | $CH_3$ | H | H | t-$C_4H_9$ | 188–190 | β |
| (Ib-17) | $CH_3$ | $CH_3$ | H | H | $CH_3$ | H | H | $CH_3$ | 218–220 | β |
| (Ib-18) | $CH_3$ | $CH_3$ | H | H | $CH_3$ | H | H | i-$C_3H_7$ | 148–150 | β |
| (Ib-19) | $CH_3$ | $CH_3$ | 6-$CH_3$ | H | $CH_3$ | $CH_3$ | H | $CH_3$ | 204 | α |
| (Ib-20) | $CH_3$ | $CH_3$ | 6-$CH_3$ | H | H | $CH_3$ | H | i-$C_3H_7$ | 173 | α |
| (Ib-21) | $CH_3$ | $CH_3$ | 6-$CH_3$ | H | H | $CH_3$ | H | t-$C_4H_9$ | 122 | α |
| (Ib-22) | $CH_3$ | $CH_3$ | H | H | H | $CH_3$ | H | $CH_3$ | 234 | α |
| (Ib-23) | $CH_3$ | $CH_3$ | H | H | H | $CH_3$ | H | i-$C_3H_7$ | 166–167 | α |
| (Ib-24) | $CH_3$ | $CH_3$ | H | H | H | $CH_3$ | H | t-$C_4H_9$ | 201 | α |
| (Ib-25) | $CH_3$ | $CH_3$ | 6-$CH_3$ | H | H | $CH_3$ | H | i-$C_3H_7$ | >220 | β |
| (Ib-26) | Cl | Cl | H | H | H | $CH_3$ | H | $CH_3$ | 201–203 | α |
| (Ib-27) | Cl | Cl | H | H | H | $CH_3$ | H | i-$C_3H_7$ | 183–185 | α |
| (Ib-28) | Cl | Cl | H | H | H | $CH_3$ | H | t-$C_4H_9$ | 183–185 | α |
| (Ib-29) | $CH_3$ | $CH_3$ | H | H | H | $CH_3$ | H | i-$C_3H_7$ | 151–152 | β |

TABLE 5-continued

| Ex. No. | X | Y | $Z_n$ | $R_a$ | $R_b$ | $R_{c1}$ | $R_{c2}$ | $R^1$ | physical const. mp.: °C. | Isomer |
|---|---|---|---|---|---|---|---|---|---|---|
| (Ib-30) | $CH_3$ | $CH_3$ | 6-$CH_3$ | H | H | $CH_3$ | H | 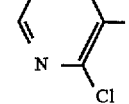 | 180 | β |
| (Ib-31) | $CH_3$ | $CH_3$ | 6-$CH_3$ | H | H | $CH_3$ | H | 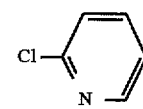 | 170–176 | β |
| (Ib-32) | $CH_3$ | $CH_3$ | 6-$CH_3$ | H | H | $CH_3$ | H | 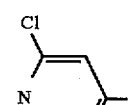 | 215 | β |
| (Ib-33) | $CH_3$ | $CH_3$ | 6-$CH_3$ | H | H | $C_2H_5$ | H | $CH_3$ | 201–202 | α |
| (Ib-34) | $CH_3$ | $CH_3$ | 6-$CH_3$ | H | H | $C_2H_5$ | H | i-$C_3H_7$ | 179–181 | α |
| (Ib-35) | Cl | Cl | H | H | H | $C_2H_5$ | H | $CH_3$ | 202–205 | α |
| (Ib-36) | Cl | Cl | H | H | H | $C_2H_5$ | H | i-$C_3H_7$ | 177–179 | α |
| (Ib-37) | Cl | Cl | H | H | H | $C_2H_5$ | H | t-$C_4H_9$ | 175–177 | α |
| (Ib-38) | Cl | Cl | H | H | H | $CH_3$ | H | $CH_3$ | 212–213 | β |
| (Ib-39) | Cl | Cl | H | H | H | $CH_3$ | H | i-$C_3H_7$ | 176–178 | β |
| (Ib-40) | Cl | Cl | H | H | H | $CH_3$ | H | t-$C_4H_9$ | 217–218 | β |
| (Ib-41) | $CH_3$ | $CH_3$ | H | H | H | $CH_3$ | H | $CH_3$ | 199–201 | β |
| (Ib-42) | $CH_3$ | $CH_3$ | H | H | H | $CH_3$ | H | t-$C_4H_9$ | 205–206 | β |
| (Ib-43) | $CH_3$ | $CH_3$ | 6-$CH_3$ | —$CH_2$— | | H | H | $CH_3$ | 225–228 | α |
| (Ib-44) | $CH_3$ | $CH_3$ | 6-$CH_3$ | —$CH_2$— | | H | H | i-$C_3H_7$ | 179–182 | α |
| (Ib-45) | Cl | Cl | H | —$CH_2$— | | H | H | i-$C_3H_7$ | 177–179 | α |
| (Ib-46) | Cl | Cl | H | —$CH_2$— | | H | H | t-$C_4H_9$ | 223–226 | α |
| (Ib-47) | Cl | Cl | H | —$CH_2$— | | H | H | $CH_3$ | 233–235 | α |
| (Ib-48) | $CH_3$ | $CH_3$ | 6-$CH_3$ | $CH_3$ | H | — | — | $CH_3$ | 210–213 | α |
| (Ib-49) | $CH_3$ | $CH_3$ | 6-$CH_3$ | $CH_3$ | H | — | — | i-$C_3H_7$ | 169–171 | α |
| (Ib-50) | $CH_3$ | $CH_3$ | 6-$CH_3$ | H | $CH_3$ | — | — | $CH_3$ | 188 | α |
| (Ib-51) | $CH_3$ | $CH_3$ | 6-$CH_3$ | H | $CH_3$ | — | — | i-$C_3H_7$ | 164 | α |
| (Ib-52) | $CH_3$ | $CH_3$ | 6-$CH_3$ | H | H | $C_6H_{11}$ | H | $CH_3$ | 222–224 | α |
| (Ib-53) | $CH_3$ | $CH_3$ | 6-$CH_3$ | H | H | $C_6H_{11}$ | H | i-$C_3H_7$ | 161–163 | α |
| (Ib-54) | $CH_3$ | $CH_3$ | 6-$CH_3$ | H | H | $C_6H_5$ | H | $CH_3$ | 224–225 | α |
| (Ib-55) | $CH_3$ | $CH_3$ | 6-$CH_3$ | H | H | $CH_3$ | $CH_3$ | $CH_3$ | >220 | — |
| (Ib-56) | $CH_3$ | $CH_3$ | 6-$CH_3$ | H | H | $CH_3$ | $CH_3$ | i-$C_3H_7$ | 217–218 | — |
| (Ib-57) | $CH_3$ | $CH_3$ | 6-$CH_3$ | H | H | $CH_3$ | $CH_3$ | t-$C_4H_9$ | >220 | — |
| (Ib-58) | $CH_3$ | $CH_3$ | 6-$CH_3$ | H | H | —$(CH_2)_5$— | | $CH_3$ | >220 | — |
| (Ib-59) | $CH_3$ | $CH_3$ | 6-$CH_3$ | H | H | —$(CH_2)_5$— | | i-$C_3H_7$ | 208–210 | — |
| (Ib-60) | $CH_3$ | $CH_3$ | 6-$CH_3$ | H | H | i-$C_3H_7$ | H | $CH_3$ | 193 | α |
| (Ib-61) | $CH_3$ | $CH_3$ | 6-$CH_3$ | H | H | i-$C_3H_7$ | H | i-$C_3H_7$ | 177–179 | α |
| (Ib-62) | $CH_3$ | $CH_3$ | 6-$CH_3$ | H | H | i-$C_3H_7$ | H | t-$C_4H_9$ | >220 | α |
| (Ib-63) | $CH_3$ | $CH_3$ | 6-$CH_3$ | H | H | $OCH_3$ | H | $CH_3$ | >220 | α |
| (Ib-64) | $CH_3$ | $CH_3$ | 6-$CH_3$ | H | H | $OCH_3$ | H | i-$C_3H_7$ | 181–182 | α |
| (Ib-65) | $CH_3$ | $CH_3$ | 6-$CH_3$ | H | H | $OCH_3$ | H | i-$C_3H_7$ | 187–189 | β |
| (Ib-66) | Cl | Cl | H | H | H | $C_2H_5$ | H | $CH_3$ | 196 | β |
| (Ib-67) | Cl | Cl | H | H | H | $C_2H_5$ | H | i-$C_3H_7$ | 172 | β |

Example (Ic-1)

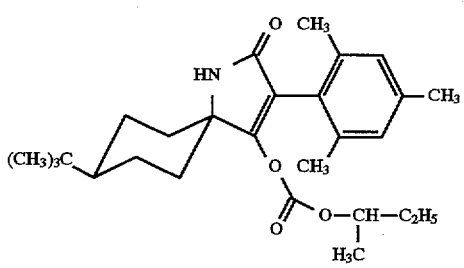

5.12 g (0.015 mol) of 3-(2,4,6-trimethylphenyl)-5,5-(4-t.-butyl)-pentamethylene-pyrrolidine-2,4-dione are dissolved in 60 ml of absolute dichloromethane and the solution is treated with 2.1 ml of triethylamine. 2.05 g of sec-butyl chloroformate in 5 ml of absolute dichloromethane are added at 0°–10° C., and stirring of the batch is continued at room temperature. The end of the reaction is determined by thin-layer chromatography. The batch is subsequently washed twice using 100 ml portions of 0.5N sodium hydroxide solution, and the organic phase is dried over magnesium sulphate. The residue obtained after evaporation of the solvent is recrystallised from ethyl acetate/n-hexane.

4.4 g (66% of theory) of 0-(sec.-butyl)-0-[3-(2,4,6-trimethylphenyl)-5,5-(4-t.-butyl)-pentamethylene-Δ3-pyrrolin-4-yl-2-one] carbonate of melting point m.p.: >220° C. (β-isomer).

Example (Ic-2)

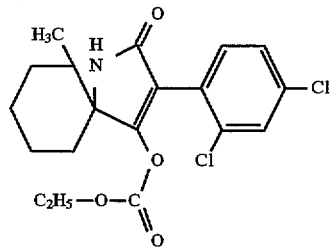

0-(sec.-butyl -0-[3-(2,46-trimethylphenyl)-5,5-(4-t.-butyl)-pentamethylene-Δ3-pyrrolin-4-yl-2-one] carboxylate of melting point m.p.: 170° C. is obtained analogously to Example (Ic-1) (isomer mixture)

The end products of the formula (Ic) listed below in Table 6 are obtained analogously to Examples (Ic-1) and (Ic-2) and following the general information in the description of the process according to the invention, as the α-isomer or the β-isomer.

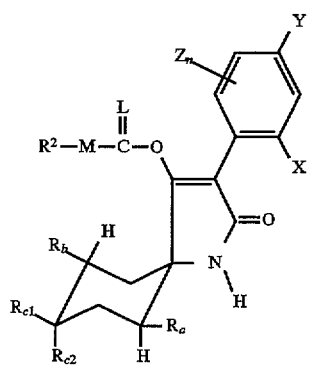

Ic
(α-isomer)

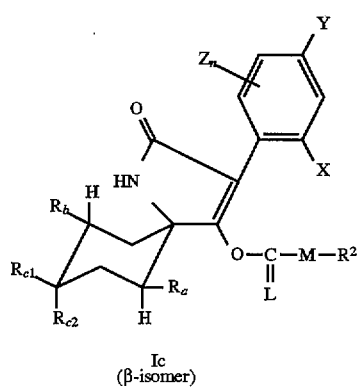

Ic
(β-isomer)

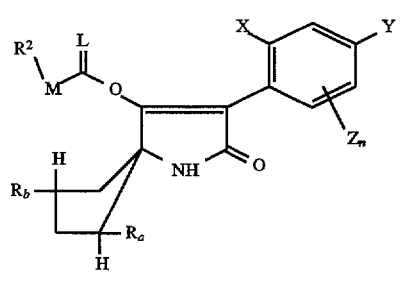

Ic
(α-isomer)

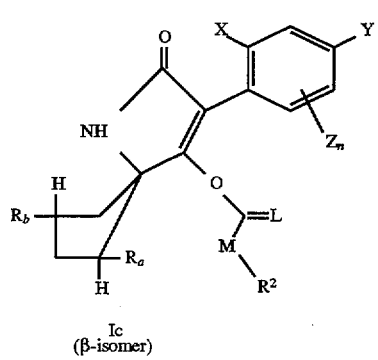

Ic
(β-isomer)

TABLE 6

| Ex. No. | X | Y | $Z_n$ | $R_a$ | $R_b$ | $R_{c1}$ | $R_{c2}$ | L | M | $R_2$ | mp.: °C. | Isomer |
|---|---|---|---|---|---|---|---|---|---|---|---|---|
| (Ic-3) | $CH_3$ | $CH_3$ | 6-$CH_3$ | $CH_3$ | H | H | H | O | O | $C_2H_5$ | 167 | α |
| (Ic-4) | $CH_3$ | $CH_3$ | 6-$CH_3$ | $CH_3$ | H | H | H | O | O | sec.-$C_4H_9$ | 188 | α |
| (Ic-5) | Cl | Cl | H | H | $CH_3$ | H | H | O | O | $C_2H_5$ | 168 | α |
| (Ic-6) | $CH_3$ | $CH_3$ | 6-$CH_3$ | H | H | $CH_3$ | H | O | O | sec.-$C_4H_9$ | >220 | β |
| (Ic-7) | Cl | Cl | H | H | $CH_3$ | H | H | O | S | $CH_2$—$C_6H_5$ | 148–150 | β |
| (Ic-8) | Cl | Cl | H | H | $CH_3$ | H | H | O | S | $CH_2$—$C_6H_5$ | 141–143 | α |
| (Ic-9) | Cl | Cl | H | H | $CH_3$ | H | H | O | S | sec.-$C_4H_9$ | 134–136 | α |
| (Ic-10) | Cl | Cl | H | H | $CH_3$ | H | H | O | S | i-$C_3H_7$ | 77–79 | α |
| (Ic-11) | Cl | Cl | H | H | $CH_3$ | H | H | O | O | sec.-$C_4H_9$ | 133 | α |
| (Ic-12) | $CH_3$ | $CH_3$ | 6-$CH_3$ | H | $CH_3$ | H | H | O | O | $C_2H_5$ | 194 | α |
| (Ic-13) | $CH_3$ | $CH_3$ | 6-$CH_3$ | H | $CH_3$ | H | H | O | O | sec.-$C_4H_9$ | 192 | α |
| (Ic-14) | $CH_3$ | $CH_3$ | 6-$CH_3$ | H | $CH_3$ | H | H | O | O | $C_2H_5$ | 190–191 | β |
| (Ic-15) | $CH_3$ | $CH_3$ | 6-$CH_3$ | H | $CH_3$ | H | H | O | O | sec.-$C_4H_9$ | >220 | β |
| (Ic-16) | Cl | Cl | H | H | $CH_3$ | H | H | O | O | $C_2H_5$ | 202–203 | β |
| (Ic-17) | Cl | Cl | H | H | $CH_3$ | H | H | O | O | sec.-$C_4H_9$ | 179–180 | β |
| (Ic-18) | $CH_3$ | $CH_3$ | H | H | $CH_3$ | H | H | O | O | $C_2H_5$ | 165–166 | β |
| (Ic-19) | $CH_3$ | $CH_3$ | H | H | $CH_3$ | H | H | O | O | sec.-$C_4H_9$ | 169–171 | β |
| (Ic-20) | $CH_3$ | $CH_3$ | 6-$CH_3$ | H | $CH_3$ | $CH_3$ | H | O | O | $C_2H_5$ | 209 | α |

TABLE 6-continued

| Ex. No. | X | Y | $Z_n$ | $R_a$ | $R_b$ | $R_{c1}$ | $R_{c2}$ | L | M | $R_2$ | mp.: °C. | Isomer |
|---|---|---|---|---|---|---|---|---|---|---|---|---|
| (Ic-21) | $CH_3$ | $CH_3$ | 6-$CH_3$ | H | $CH_3$ | $CH_3$ | H | O | O | sec.-$C_4H_9$ | 171 | α |
| (Ic-22) | $CH_3$ | $CH_3$ | H | H | H | $CH_3$ | H | O | O | $C_2H_5$ | 151 | α |
| (Ic-23) | $CH_3$ | $CH_3$ | H | H | H | $CH_3$ | H | O | O | sec.-$C_4H_9$ | 144 | α |
| (Ic-24) | $CH_3$ | $CH_3$ | 6-$CH_3$ | H | H | $CH_3$ | H | O | O | $C_2H_5$ | >220 | β |
| (Ic-25) | Cl | Cl | H | H | H | $CH_3$ | H | O | O | $C_2H_5$ | 170–173 | α |
| (Ic-26) | Cl | Cl | H | H | H | $CH_3$ | H | O | O | sec.-$C_4H_9$ | 146–148 | α |
| (Ic-27) | $CH_3$ | $CH_3$ | 6-$CH_3$ | H | H | $C_2H_5$ | H | O | O | $C_2H_5$ | 166–168 | α |
| (Ic-28) | $CH_3$ | $CH_3$ | 6-$CH_3$ | H | H | $C_2H_5$ | H | O | O | sec.-$C_4H_9$ | 199–203 | α |
| (Ic-29) | Cl | Cl | H | H | H | $C_2H_5$ | H | O | O | $C_2H_5$ | 188–190 | α |
| (Ic-30) | Cl | Cl | H | H | H | $C_2H_5$ | H | O | O | sec.-$C_4H_9$ | 171–173 | α |
| (Ic-31) | Cl | Cl | H | H | H | $CH_3$ | H | O | O | $C_2H_5$ | 197–198 | β |
| (Ic-32) | Cl | Cl | H | H | H | $CH_3$ | H | O | O | sec.-$C_4H_9$ | 227–228 | α |
| (Ic-33) | $CH_3$ | $CH_3$ | H | H | H | $CH_3$ | H | O | O | i-$C_3H_7$ | 202–204 | β |
| (Ic-34) | $CH_3$ | $CH_3$ | H | H | H | $CH_3$ | H | O | O | $C_2H_5$ | 193–194 | β |
| (Ic-35) | $CH_3$ | $CH_3$ | H | H | H | $CH_3$ | H | O | O | sec.-$C_4H_9$ | 168–169 | β |
| (Ic-36) | $CH_3$ | $CH_3$ | 6-$CH_3$ | H | H | $CH_3$ | H | O | O | $CH_3$ | 206 | β |
| (Ic-37) | $CH_3$ | $CH_3$ | 6-$CH_3$ | H | H | $CH_3$ | H | O | O | i-$C_3H_7$ | >220 | β |
| (Ic-38) | $CH_3$ | $CH_3$ | 6-$CH_3$ | —$CH_2$— | | H | H | O | O | $C_2H_5$ | 183–186 | α |
| (Ic-39) | $CH_3$ | $CH_3$ | 6-$CH_3$ | —$CH_2$— | | H | H | O | O | sec.-$C_4H_9$ | 159–161 | α |
| (Ic-40) | Cl | Cl | H | —$CH_2$— | | H | H | O | O | $C_2H_5$ | 153–155 | α |
| (Ic-41) | Cl | Cl | H | —$CH_2$— | | H | H | O | O | sec.-$C_4H_9$ | 155–157 | α |
| (Ic-42) | $CH_3$ | $CH_3$ | 6-$CH_3$ | $CH_3$ | H | — | — | O | O | $C_2H_5$ | 173–176 | α |
| (Ic-43) | $CH_3$ | $CH_3$ | 6-$CH_3$ | $CH_3$ | H | — | — | O | O | sec.-$C_4H_9$ | 186–189 | α |
| (Ic-44) | $CH_3$ | $CH_3$ | 6-$CH_3$ | H | $CH_3$ | — | — | O | O | $C_2H_5$ | 194 | α |
| (Ic-45) | $CH_3$ | $CH_3$ | 6-$CH_3$ | H | $CH_3$ | — | — | O | O | sec.-$C_4H_9$ | 187 | α |
| (Ic-46) | $CH_3$ | $CH_3$ | 6-$CH_3$ | H | H | $C_6H_{11}$ | H | O | O | $C_2H_5$ | 155–156 | α |
| (Ic-47) | $CH_3$ | $CH_3$ | 6-$CH_3$ | H | H | $C_6H_{11}$ | H | O | O | sec.-$C_4H_9$ | 185–186 | α |
| (Ic-48) | $CH_3$ | $CH_3$ | 6-$CH_3$ | H | H | $C_6H_5$ | H | O | O | $C_2H_5$ | 225–226 | α |
| (Ic-49) | $CH_3$ | $CH_3$ | 6-$CH_3$ | H | H | $C_6H_5$ | H | O | O | sec.-$C_4H_9$ | 109–199 | α |
| (Ic-50) | $CH_3$ | $CH_3$ | 6-$CH_3$ | H | H | $CH_3$ | $CH_3$ | O | O | $C_2H_5$ | >220 | — |
| (Ic-51) | $CH_3$ | $CH_3$ | 6-$CH_3$ | H | H | $CH_3$ | $CH_3$ | O | O | sec.-$C_4H_9$ | 220–221 | — |
| (Ic-52) | $CH_3$ | $CH_3$ | 6-$CH_3$ | H | H | —($CH_2$)5— | | O | O | $C_2H_5$ | 227–229 | — |
| (Ic-53) | $CH_3$ | $CH_3$ | 6-$CH_3$ | H | H | —($CH_2$)5— | | O | O | sec.-$C_4H_9$ | 206–208 | — |
| (Ic-54) | $CH_3$ | $CH_3$ | 6-$CH_3$ | H | H | i-$C_3H_7$ | H | O | O | $C_2H_5$ | 143 | α |
| (Ic-55) | $CH_3$ | $CH_3$ | 6-$CH_3$ | H | H | i-$C_3H_7$ | H | O | O | sec.-$C_4H_9$ | 177–179 | α |
| (Ic-56) | $CH_3$ | $CH_3$ | 6-$CH_3$ | H | H | $OCH_3$ | H | O | O | $C_2H_5$ | 182 | α |
| (Ic-57) | $CH_3$ | $CH_3$ | 6-$CH_3$ | H | H | $OCH_3$ | H | O | O | $C_2H_5$ | 154 | β |
| (Ic-58) | $CH_3$ | $CH_3$ | 6-$CH_3$ | H | H | $C_2H_5$ | H | O | O | $C_2H_5$ | 236 | β |
| (Ic-59) | $CH_3$ | $CH_3$ | 6-$CH_3$ | H | H | $C_2H_5$ | H | O | O | sec.-$C_4H_9$ | 179 | β |
| (Ic-60) | Cl | Cl | H | H | H | $C_2H_5$ | H | O | O | $C_2H_5$ | 204 | β |
| (Ic-61) | Cl | Cl | H | H | H | $C_2H_5$ | H | O | O | sec.-$C_4H_9$ | 198 | β |

Example (Id-1)

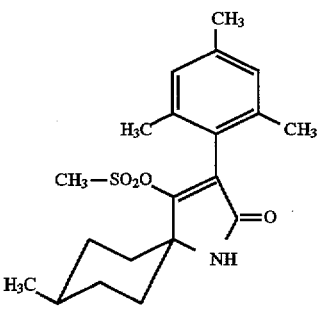

5.99 g (0.02 mol) 3-(2,4,6-trimethylphenyl)-5,5-(4-methyl)-pentamethylene-pyrrolidine-2,4-dione are dissolved in 70 ml of absolute dichloromethane and the solution is treated with 2.8 ml of triethylamine. 2.29 g of methane sulphonyl chloride in 5 ml of absolute dichloromethane are added dropwise at 0° C. to 10° C. The end of the reaction is determined by thin-layer chromatography. The mixture is subsequently washed twice using 200 ml portions of 0.5N sodium hydroxide solution and the organic phase is dried over magnesium sulphate. After the solvent has been removed and the residue has been suspended in ethyl acetate, 3.1 g (41% of theory) of 3-(2,4,6-trimethylphenyl-5,5-(4-methyl)-pentamethylene-4-methylsulphonyloxy-Δ3-pyrrolin-2-one of melting point m.p.: 205°–206° C. are obtained. (α-isomer)

Example (Ie-1) (α-Isomer)

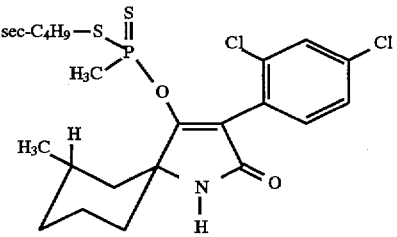

2 g (6.2 mmol) 3-(2,4-dichlorphenyl)-5,5-(3-methyl)-pentamethylen-pyrrolidin-2,4-dion are suspended in 20 ml of absolute tetrahydrofurane and treated with 1 ml of triethylamine. After addition of 1,5 g (7 mmol) of methyl-sec-butylthiophoshonic-acidchloride the mixture is stirred overnight. The solvent is evaporated and the residue separated chromatographically with cyclohexane/ethylacetate 2:1 on silicagel. 1.7 g (37 % of theory) of the above mentioned compound (α-isomer, melting point 69 ° C.) are obtained.

Example (If-1)

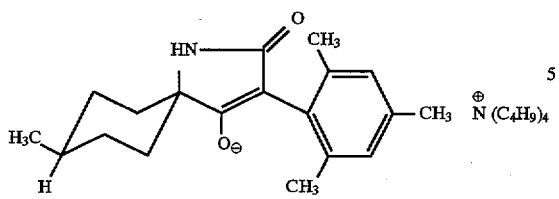

2.99 g (10mmol) 3-(2,4-6-trimethylphenyl)-5,5-(4-methyl)-pentamethylen-pyrrolidin-2,4-dion are suspended in 40 ml of absolute methylenchloride. After addition of 6,24 g tetrabutylammoniumhydroxide (40% aqueous solution) the mixture is stirred for minutes, the solvent is evaporated and the residue crystallized with diisopropylether. 5.1 g (94% of theory) of the above mentioned compound (melting point 125° C., β-isomer) are obtained.

Example (If-2)

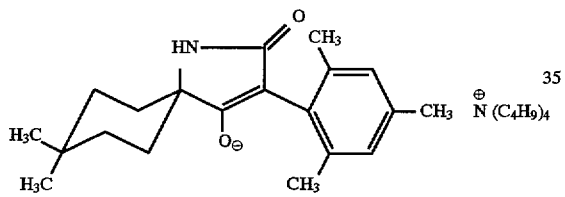

Analogously compound If-2 of melting point 110 ° C. is obtained.

Example (Ig-1)

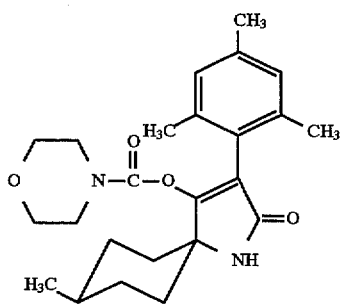

5.99 g (0.02 mol) of 3-(2,4,6-trimethylphenyl)-5,5-(4-methyl)-pentamethylene-pyrrolidine-2,4-dione are dissolved in 70 ml of absolute dichloromethane and the solution is treated with 2.8 ml of triethylamine. 2.34 ml of morpholinecarbamoyl chloride in 5 ml of dichloromethane are added at 0° to 10° C. and stirring of the batch is continued at room temperature until, according to check by thin-layer chromatography, the reaction has ended. The mixture is then washed twice using 200 ml portions of 0.5N sodium hydroxide solution and the organic phase is dried over magnesium sulphate. After the solvent has been evaporated and the residue suspended in ethyl acetate, 2.3 g (28% of theory) of 3-(2,4,6-trimethylphenyl)-5,5-(4-methyl)-pentamethylene-4-(morpholinecarb moyl)-Δ3-pyrrolin-2-one of melting point m.p.: 197°–198° C. are obtained. (α-isomer).

Example (Ig-2)

Analogously 3-(2,4,6-trimethylphenyl)-5,5-(4-methyl) pentamethylene-4-(morpholincarbamoyl)-Δ3-pyrrolin-2-on (melting point 189°–193° C.); β-isomer) are obtained.

Analogously are obtained:

TABLE 7

| Ex Nr.: | X | Y | Zn | $R_a$ | $R_b$ | $R_{c1}$ | $R_{c2}$ | L | $R^7$ | $R^8$ | mp °C. | isomer |
|---|---|---|---|---|---|---|---|---|---|---|---|---|
| (Ig-3) | CH₃ | CH₃ | H | H | H | CH₃ | H | O | —(CH₂)₂—O—(CH₂)₂— | | >220 | β |
| (Ig-4) | CH₃ | CH₃ | H | H | H | CH₃ | H | O | CH₃ | CH₃ | >220 | β |
| (Ig-5) | CH₃ | CH₃ | 6-CH₃ | H | H | CH₃ | CH₃ | O | —(CH₂)₂—O—(CH₂)₂— | | 167 | — |

Preparation of the starting compounds

Example (II-1)

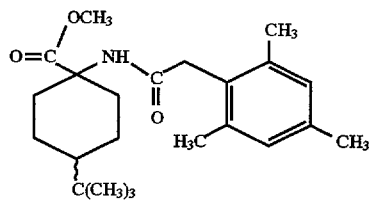

29.1 g (0.117 mol) of 4-(t-butyl)-methyl 1-amino-1-cyclohexanecarboxylate hydrochloride are dissolved in 300 ml of tetrahydorfuran and the solution is treated with 34.4 ml (0.246 mol) of triethylamine. 23 g of mesityleneacetyl chloride in 20 ml of absolute tetrahydrofuran are added dropwise at 0° to 10° C. and stirring off the batch is continued at room temperature. The end of the reaction is determined by thin-layer chromatography. The batch is stirred into 0.5 l of ice-water with 100 ml of 1N hydrochloric acid, and the mixture is extracted using dichloromethane. After the mixture has been washed with sodium hydrogen carbonate solution and after the organic phase has been dried, the solvent is stripped off. The crude product is recrystallised from toluene/n-hexane. 25.6 g (59% of theory) of methyl N-(2,4,6-tri-methylphenylacetyl)-1-amino-4.tert.-butyl-cyclohexane-carboxylate of melting point m.p.: 153°–154° C. (β-isomer) are obtained.

Example (II-2)

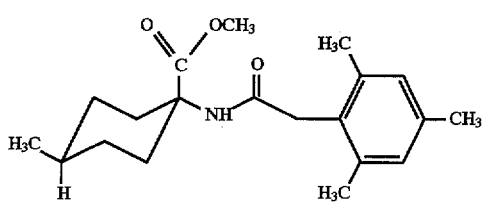

To 148 g (1.52 mol) of conc. sulphuric acid is added dropwise a solution of 90.9 g (0.30 mol) N-(2,4,6-trimethylphenylacetyl)-4-methyl-1-amino-cyclohexane-nitrile in 600 ml methylene chloride at a temperatur of 30°–40° C. After 2 h 212 ml of abs. methanol are added dropwise at 40° C. and the mixture is stirred for 6 h at 40°–70° C.

Then the reaction mixture is poured into ice water and extracted with methylene chloride. The organic phase is washed with aequous NaHCO₃, dried and evaporated. The product is purified by recristallisation from toluene/n-hexane.

Yield: 73.9 g (73% of theory) of methyl N-(2,4,6-trimethylphenyl-acetyl)-4-methyl-1-amino-cyclohexanecarboxylate of melting point m.p.: 146° C.

The starting compounds of the formula (II) listed below in Table 7 are obtained analogously to Example (II-1) and following the general information in the description for the processes according to the invention, in the form of isomer mixtures.

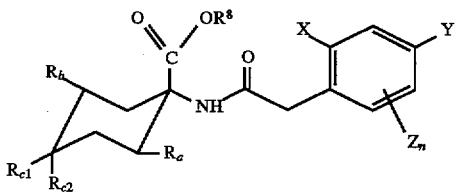

II
(α-Isomer)

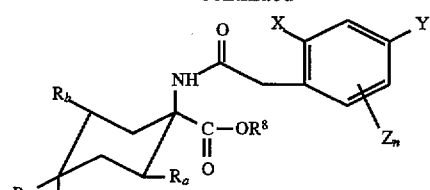

II
(β-Isomer)

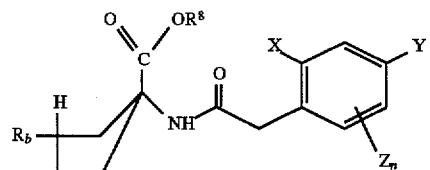

II
(α-Isomer)

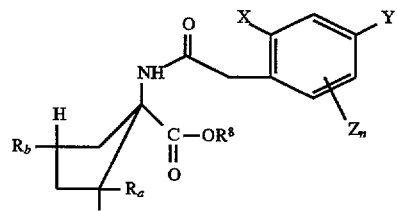

II
(β-Isomer)

TABLE 8

| Ex. No. | $R_a$ | $R_b$ | $R_{c1}$ | $R_{c2}$ | X | Y | $Z_n$ | $R^8$ | phys. const. mp.: °C. | Isomer |
|---|---|---|---|---|---|---|---|---|---|---|
| (II-2) | H | H | CH₃ | H | CH₃ | CH₃ | 6-CH₃ | CH₃ | 146 | α |
| (II-3) | H | H | CH₃ | H | Cl | Cl | H | CH₃ | 118 | α |
| (II-4) | H | H | CH₃ | H | CH₃ | CH₃ | 6-CH₃ | CH₃ | 149–151 | β |
| (II-5) | CH₃ | H | H | H | CH₃ | CH₃ | 6-CH₃ | CH₃ | 103–104 | α |
| (II-6) | CH₃ | H | H | H | Cl | Cl | H | CH₃ | 156 | α |
| (II-7) | H | CH₃ | H | H | CH₃ | CH₃ | 6-CH₃ | CH₃ | 123–124 | β |
| (II-8) | H | CH₃ | H | H | Cl | Cl | H | CH₃ | 144 | α |
| (II-9) | H | H | CH₃ | CH₃ | CH₃ | CH₃ | 6-CH₃ | CH₃ | 142 | — |
| (II-10) | H | CH₃ | H | H | CH₃ | CH₃ | 6-CH₃ | CH₃ | 160 | α |
| (II-11) | H | H | CH₃ | H | CH₃ | CH₃ | H | CH₃ | 127–128 | α |
| (II-12) | H | CH₃ | CH₃ | H | CH₃ | CH₃ | 6-CH₃ | CH₃ | 147 | α |
| (II-13) | H | CH₃ | CH₃ | H | Cl | Cl | H | CH₃ | 138 | α |
| (II-14) | H | H | i-C₃H₇ | H | CH₃ | CH₃ | 6-CH₃ | CH₃ | 137–139 | α |
| (II-15) | H | H | C₂H₅ | H | Cl | Cl | H | CH₃ | 103–105 | α |
| (II-16) | H | H | C₂H₅ | H | CH₃ | CH₃ | 6-CH₃ | CH₃ | 144–145 | α |
| (II-17) | H | H | C₂H₅ | H | CH₃ | CH₃ | 6-CH₃ | CH₃ | 129–130 | β |
| (II-18) | H | H | OCH₃ | H | CH₃ | CH₃ | 6-CH₃ | CH₃ | 116–118 | α |
| (II-19) | H | H | C₆H₁₁ | H | CH₃ | CH₃ | 6-CH₃ | CH₃ | 208–210 | α |
| (II-20) | H | H | C₆H₅ | H | CH₃ | CH₃ | 6-CH₃ | CH₃ | 207 | α |

TABLE 8-continued

| Ex. No. | $R_a$ | $R_b$ | $R_{c1}$ | $R_{c2}$ | X | Y | $Z_n$ | $R^8$ | phys. const. mp.: °C. | Isomer |
|---|---|---|---|---|---|---|---|---|---|---|
| (II-21) | H | H | —(CH$_2$)$_5$— | | CH$_3$ | CH$_3$ | 6-CH$_3$ | CH$_3$ | 153–154 | — |
| (II-22) | H | CH$_3$ | H | H | Cl | Cl | H | CH$_3$ | 147–148 | β |
| (II-23) | H | H | CH$_3$ | H | Cl | Cl | H | CH$_3$ | 151–152 | β |
| (II-24) | H | H | CH$_3$ | H | CH$_3$ | CH$_3$ | H | CH$_3$ | 123–124 | β |
| (II-25) | H | CH$_3$ | H | H | CH$_3$ | CH$_3$ | H | CH$_3$ | 131 | β |
| (II-26) | H | H | C$_2$H$_5$ | H | Cl | Cl | H | CH$_3$ | 106 | β |
| (II-27) | H | CH$_3$ | — | — | CH$_3$ | CH$_3$ | 6-CH$_3$ | CH$_3$ | 83–85 | α |
| (II-28) | CH$_3$ | H | — | — | CH$_3$ | CH$_3$ | 6-CH$_3$ | CH$_3$ | 107–108 | α |
| (II-29) | H | H | C$_2$H$_5$ | H | CH$_3$ | CH$_3$ | H | CH$_3$ | 105 | β |
| (II-30) | H | H | C$_3$H$_7$ | H | CH$_3$ | CH$_3$ | 6-CH$_3$ | CH$_3$ | 155 | β |
| (II-31) | H | H | C$_3$H$_7$ | H | CH$_3$ | CH$_3$ | H | CH$_3$ | 131 | β |
| (II-32) | H | H | C$_3$H$_7$ | H | | | H | CH$_3$ | 106 | β |
| (II-33) | H | H | i-C$_3$H$_7$ | H | CH$_3$ | CH$_3$ | 6-CH$_3$ | CH$_3$ | 145 | β |
| (II-34) | H | H | i-C$_3$H$_7$ | H | CH$_3$ | CH$_3$ | H | CH$_3$ | 118 | β |

Examples for the preparation of the starting compounds of the formula XVII:

Example XVII-1

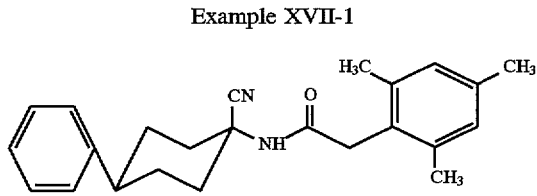

To 40 g (0.2 mol) of 1-amino-4-phenyl-cyclohexanecarboxylic acid nitrile and 28 ml (0.2 mol) of triethylamine in 450 ml of absolute tetrahydrofuran there are added dropwise with stirring at 0° C. to 10° C. 39.3 g (0.2 mol) of mesityleneacetyl chloride (compare, for example, Tetrahedron 31, 2691–2694 [1975]) in 40 ml of absolute tetrahydrofuran, and, when the addition has ended, the mixture is stirred at room temperature until starting material can no longer be detected in a thin-layer chromatogram. For working-up, the reaction mixture is added with stirring to a mixture of 1000 ml of ice-water and 200 ml of 1N hydrochloric acid, solid which has precipitated is filtered off with suction, the residue is dissolved in dichloromethane, the aqueous phase is separated, the organic phase is dried over magnesium sulphate and the solvent is removed in vacuo. 65 g (91% of theory) of N-(2,4,6-trimethylphenyl-acetyl-4-phenylcyclohexanecarboxylic nitrile of melting point 235°–238° C.) are obtained.

The following compounds XVII are obtained analogously and following the general information on the preparation:

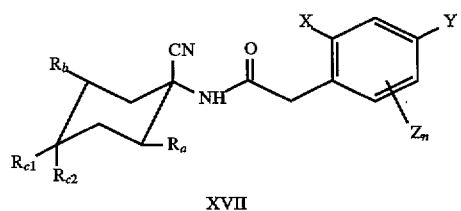

XVII

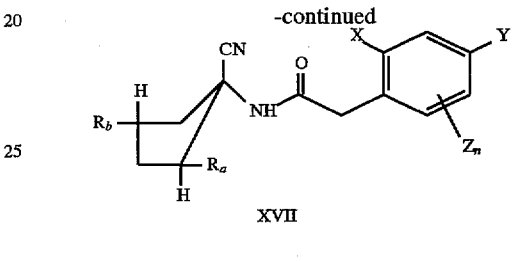

XVII

TABLE 9

| Ex. No. | $R_a$ | $R_b$ | $R_{c1}$ | $R_{c2}$ | X | Y | $Z_n$ | mp.: °C. |
|---|---|---|---|---|---|---|---|---|
| XVII-2 | CH$_3$ | H | H | H | CH$_3$ | CH$_3$ | 6-CH$_3$ | 183–184 |
| XVII-3 | CH$_3$ | H | H | H | Cl | Cl | H | 153 |
| XVII-4 | H | H | CH$_3$ | H | CH$_3$ | CH$_3$ | 6-CH$_3$ | 202 |
| XVII-5 | H | H | CH$_3$ | H | Cl | Cl | H | 203 |
| XVII-6 | H | CH$_3$ | H | H | Cl | Cl | H | 189 |
| XVII-7 | H | CH$_3$ | H | H | CH$_3$ | CH$_3$ | 6-CH$_3$ | 176 |
| XVII-8 | H | CH$_3$ | CH$_3$ | H | CH$_3$ | CH$_3$ | 6-CH$_3$ | 174 |
| XVII-9 | H | CH$_3$ | CH$_3$ | H | Cl | Cl | H | 153 |
| XVII-10 | H | H | CH$_3$ | H | CH$_3$ | CH$_3$ | H | 198 |
| XVII-11 | H | H | i-C$_3$H$_7$ | H | CH$_3$ | CH$_3$ | 6-CH$_3$ | 204–206 |
| XVII-12 | H | H | C$_2$H$_5$ | H | CH$_3$ | CH$_3$ | 6-CH$_3$ | 185 |
| XVII-13 | H | H | C$_2$H$_5$ | H | Cl | Cl | H | 194 |
| XVII-14 | H | H | CH$_3$ | CH$_3$ | CH$_3$ | CH$_3$ | 6-CH$_3$ | 190–192 |
| XVII-15 | H | H | OCH$_3$ | H | CH$_3$ | CH$_3$ | 6-CH$_3$ | 159–160 |
| XVII-16 | H | H | C$_6$H$_{11}$ | H | CH$_3$ | CH$_3$ | 6-CH$_3$ | 208 |
| XVII-17 | H | H | —(CH$_2$)$_5$— | | CH$_3$ | CH$_3$ | 6-CH$_3$ | 198–201 |
| XVII-18 | H | CH$_3$ | — | — | CH$_3$ | CH$_3$ | 6-CH$_3$ | 139 |
| XVII-19 | CH$_3$ | H | — | — | CH$_3$ | CH$_3$ | 6-CH$_3$ | 142 |

Example A

Phaedon larvae test

Solvent: 7 parts by weight of diemethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (*Phaedon cochleariae*), while the leaves are still moist.

After the specified period of time, the destruction in % is determined. 100% means that all the beetle larvae have been killed; 0% means that none of the beetle larvae have been killed.

In this test, a superior activity compared with the prior art is shown, for example, for the following compounds of the preparation examples: (Ia-10), (Ia-11), (Ib-11), (Ib-12), (Ig-1).

Example B

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, a superior activity compared with the prior art is shown, for example, for the following compounds of the preparation examples: (Ia-10), (Ia-11), (Ib-12), (Ig-1).

Example C

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice cicada (*Nephotettix cincticeps*) while the leaves are still moist.

After the specified period of time, the destruction in % is determined. 100% means that all the cicadas have been killed; 0% means that none of the cicadas have been killed.

In this test, a superior activity compared with the prior art is shown, for example, for the following compounds of the preparation examples: (Ia-10), (Ia-11), (Ib-11), (Ib-12) (Ig-1).

Example D

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the cencentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

A clearly superior activity and crop plant selectivity compared with the prior art is shown, in this test, for example by the compounds of preparation example: (Ia-10), (Ia-11), (Ib-12), (Ib-11), (Ic-6).

Example E

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Test plants which have a height of 5–15 cm are sprayed with the preparation of the active compound in such a way as to apply the particular amounts of active compound desired per unit area. After three weeks, the degree of damage to the plants is rated in % damage in comparison to the development of the untreated control. The figures denote:

0%=no action (like untreated control)
100%=total destruction

A clearly superior activity and crop plant selectivity compared with the prior art is shown, in this test, for example by the compounds of preparation example: (Ia-10), (Ia-11), (Ib-11), (Ib-12).

We claim:

1. A compound of the formula

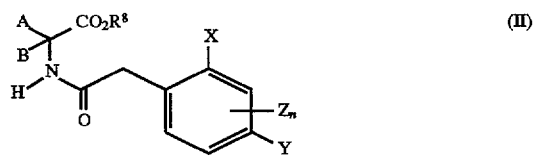

(II)

in which

A and B together with the carbon atom to which they are bonded represent a substituted cycle, X represents alkyl, halogen or alkoxy, Y represents hydrogen, alkyl, halogen, alkoxy or halogenoalkyl, Z represents alkyl, halogen or alkoxy, n represents 0, 1, 2 or 3, and $R^8$ represents alkyl.

2. Process for the preparation of the compounds of the formula (II), according to claim 1 characterized in that amino acid derivatives of the formula (XIV)

(XIV)

in which $R^{9'}$ represents hydrogen (XIVa) and alkyl (XIVb) and

A and B have the meaning given in claim 1 are acylated with phenylacetyl halides of the formula (XV)

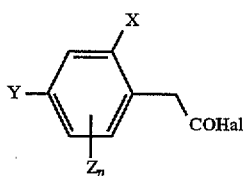

in which

X, Y, Z and n have the meaning given in claim 1 and HAL represents chlorine or bromine or acylamine acids of the formula (IIa)

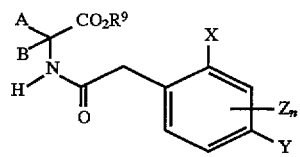

in which

A, B, X, Y, Z and n have the meaning given in claim 1 and $R^{9'}$ represents hydrogen are esterfied, or aminonitriles of the formula (XVI)

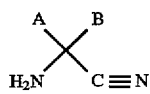

in which

A and B have the abovementioned meaning are reacted with phenylacetyl halides of the formula (XV)

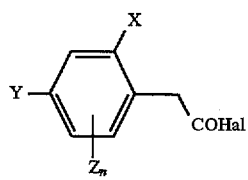

in which

X, Y, Z and n have the abovementioned meaning and Hal represents chlorine or bromine to give compounds of the formula (XVII)

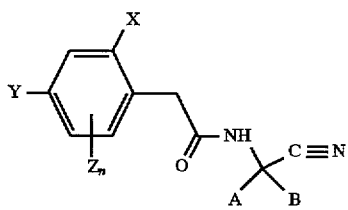

in which

A, B, X, Y, Z and n have the abovementioned meaning and these compounds are subsequently subjected to alcoholysis in sulphuric acid.

3. The compound according to claim 1 in which

A, B and the carbon atom to which they are bonded represent a $C_3-C_6$-spirocycle which can be monosubstituted or polysubstituted by $C_1-C_6$-alkyl, $C_3-C_8$-cycloalkyl, $C_1-C_3$-haloalkyl, $C_1-C_4$-alkoxy, $C_1-C_4$-thioalkyl, fluorine, chlorine or phenyl, or A, B and the carbon atom to which they are bonded represent a $C_3-C_6$-spirocycle which is substituted by an alkylenediyl group which is optionally interrupted by one or two oxygen or sulphur atoms or by an alkylenedioxyl or an alkylenedithiooxyl group which, together with the carbon atom to which it is bonded, forms a further five- to seven-membered spirocycle, or A, B and the carbon atom to which they are bonded represent a $C_3-C_6$-spirocycle in which two substituents together with the C-atoms to which they are bonded represent a saturated or unsaturated carbocyle which is substituted by alkyl($C_1-C_3$), alkoxy($C_1-C_3$), or fluorine, chlorine or bromine and which is optionally interrupted by oxygen or sulphur atom, X represents $C_1-C_4$-alkyl, halogen or $C_1-C_4$-alkoxy, Y represents hydrogen, methyl, ethyl, propyl, i-propyl, butyl, i-butyl, fluorine, chlorine, bromine, methoxy, ethoxy or trifluoromethyl, Z represents methyl, ethyl, prapyl, i-propyl, butyl, i-butyl, tert.-butyl, fluorine, chlorine, bromine, methoxy or ethoxy, represents 0, 1 or 2.

4. The compound according to claim 1, in which

A, B and the carbon atom to which they are bonded represent a $C_3-C_6$ -spirocycle which can be at least monosubstituted or polysubstituted by methyl, ethyl, propyl, isopropyl, butyl, iso-butyl, sec.-butyl, tert,-butyl, cyclohexyl, trifluoromethyl, methoxy, methylthio, fluorine, chlorine or phenyl, or A, B and the carbon atom to which they are bonded represent a $C_3-C_6$-spirocycle which is substituted by an alkylenediyl group which is optionally interrupted by an oxygen or sulphur atom or by an alkylenedioxyl group which group, together with the carbon atom to which it is bonded, forms a further five- to seven-membered spirocycle, A, B and the carbon atom to which they are bonded represent a $C_3-C_6$-spirocycle in which two substituents together with the carbon atoms to which they are bonded represent a saturated or unsaturated five- or six-membered cycle, which is optionally interrupted by oxygen or sulphur, X represents methyl, ethyl, propyl, 2-propyl, fluorine, chlorine, bromine, methoxy or ethoxy, Y represents hydrogen, methyl, ethyl, propyl, i-propyl, butyl, i-butyl, tert.-butyl, fluorine, chlorine, bromine, methoxy, ethoxy or tri-fluoromethyl, Z represents methyl, ethyl, propyl, i-propyl, butyl, i-butyl, tert.-butyl, fluorine, chlorine, bromine, methoxy or ethoxy, n represents 0 or 1.

* * * * *

UNITED STATES PATENT AND TRADEMARK OFFICE
CERTIFICATE OF CORRECTION

PATENT NO. : 5,677,449
DATED : October 14, 1997
INVENTOR(S) : Fischer, et al.

It is certified that error appears in the above-indentified patent and that said Letters Patent is hereby corrected as shown below:

Col. 72, line 24  Delete " prapyl " and substitute -- propyl --

Signed and Sealed this

Twenty-third Day of June, 1998

BRUCE LEHMAN

Attest:

Attesting Officer    Commissioner of Patents and Trademarks